United States Patent
Sarvazyan

[11] Patent Number: 5,836,894
[45] Date of Patent: *Nov. 17, 1998

[54] APPARATUS FOR MEASURING MECHANICAL PARAMETERS OF THE PROSTATE AND FOR IMAGING THE PROSTATE USING SUCH PARAMETERS

[75] Inventor: Armen P. Sarvazyan, E. Brunwick, N.J.

[73] Assignee: Artann Laboratories, Lambertville, N.J.

[ * ] Notice: The term of this patent shall not extend beyond the expiration date of Pat. No. 5,785,663.

[21] Appl. No.: 872,561

[22] Filed: Jun. 10, 1997

Related U.S. Application Data

[63] Continuation-in-part of Ser. No. 607,645, Feb. 27, 1996, which is a continuation-in-part of Ser. No. 994,109, Dec. 21, 1992, Pat. No. 5,524,636.

[51] Int. Cl.⁶ .......................................................... A61B 5/00
[52] U.S. Cl. .......................................... 600/587; 600/561
[58] Field of Search .................................... 600/486, 488, 600/561, 587

[56] References Cited

U.S. PATENT DOCUMENTS

| | | | |
|---|---|---|---|
| 4,711,248 | 12/1987 | Steuer et al. | 600/561 |
| 4,722,348 | 2/1988 | Ligtenberg et al. | 600/488 |
| 4,809,710 | 3/1989 | Williamson | 600/561 |
| 4,869,265 | 9/1989 | McEwen | 600/561 |
| 4,893,634 | 1/1990 | Kulik et al. | 600/561 |
| 5,067,491 | 11/1991 | Taylor, II et al. | 600/561 |
| 5,522,399 | 6/1996 | Wilk et al. | 600/561 |
| 5,526,820 | 6/1996 | Khoury | 600/561 |

*Primary Examiner*—Robert L. Nasser
*Attorney, Agent, or Firm*—Mathews, Collins, Shepard & Gould, P.A.

[57] ABSTRACT

A pressure force sensing array is used to measure the surface stress pattern on soft tissues. The pattern of mechanical stress and the changes in the pattern as a function of the applied pressure, position of the array and time are processed to construct an image of the internal structure of the tissues. The detected parameters and processed image provide information useful in the detection and diagnosis of soft tissue pathologies such as breast and prostate tumors. The present invention relates to an apparatus particularly useful for mechanical imaging of the prostate which comprises a transrectal probe. The probe includes a probe shaft, a position sensor for determining the position of the tip and an array of force sensors for determining the pattern of pressure from tissue deformed by the tip.

9 Claims, 20 Drawing Sheets

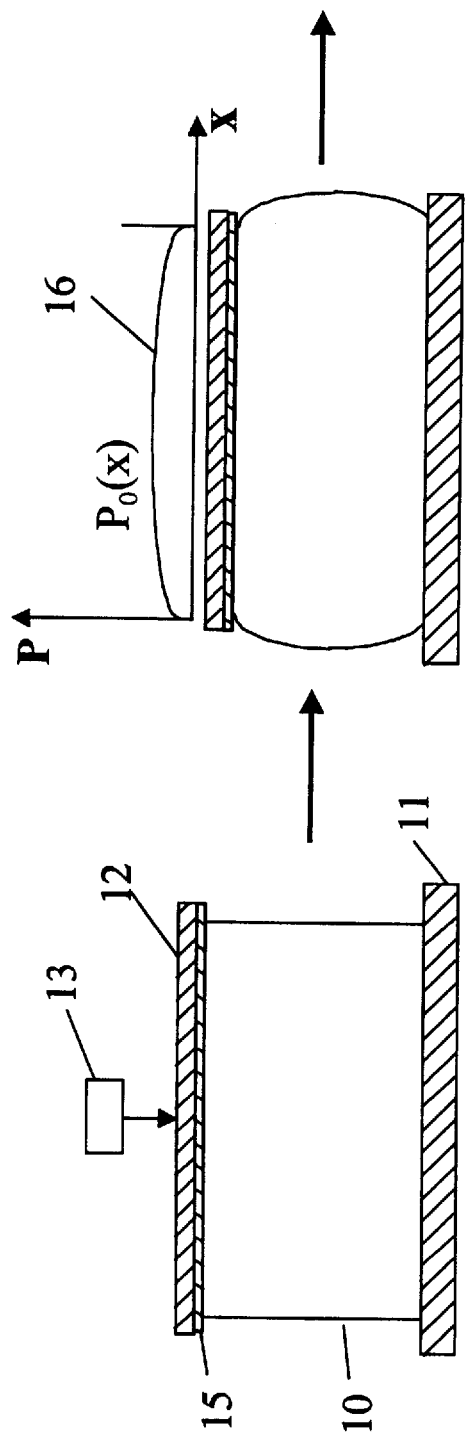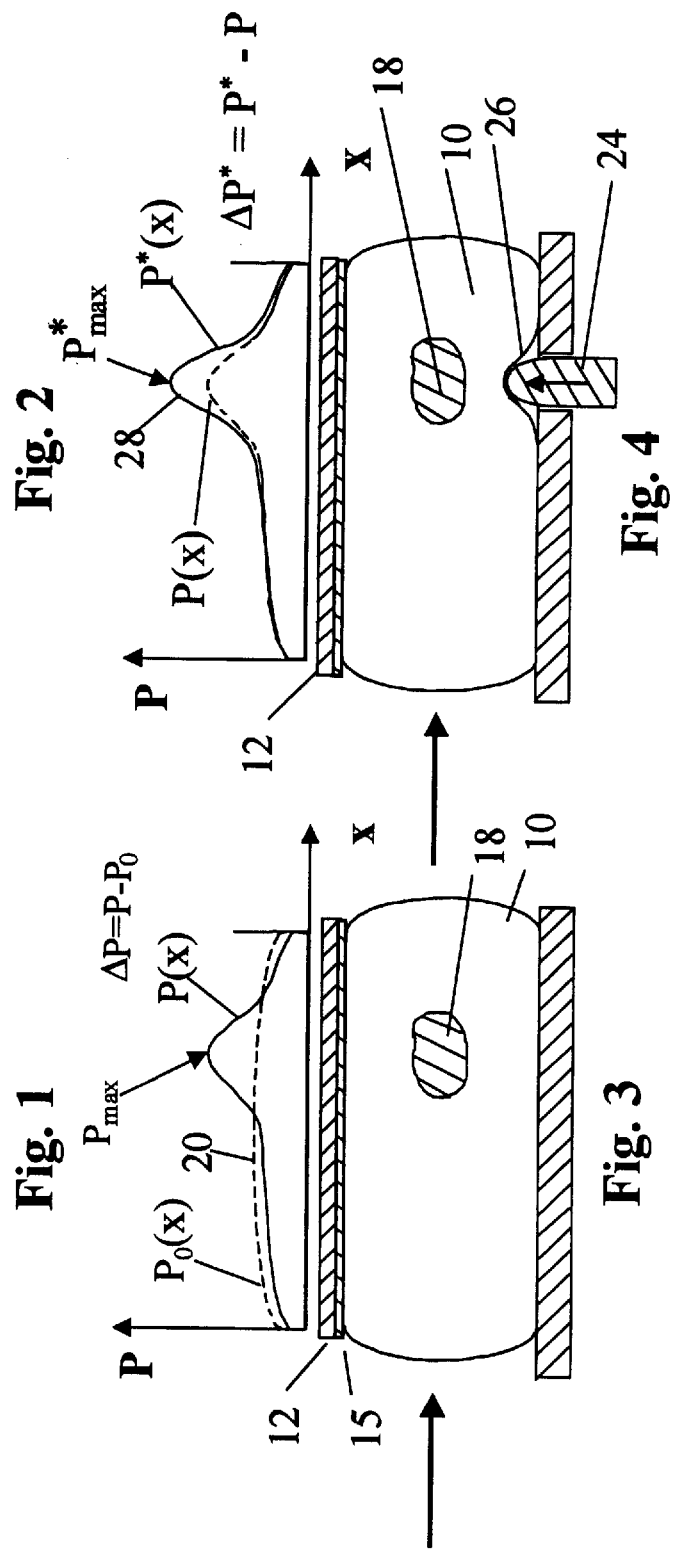

Fig. 11A
Fig. 11B
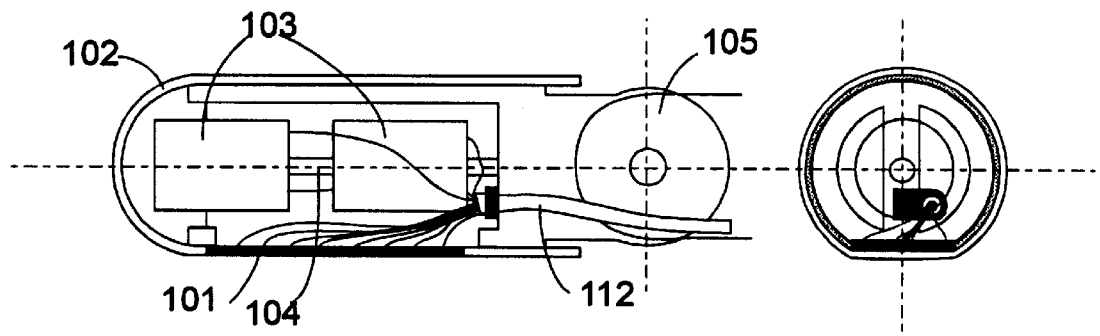
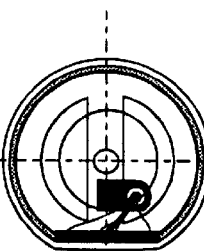
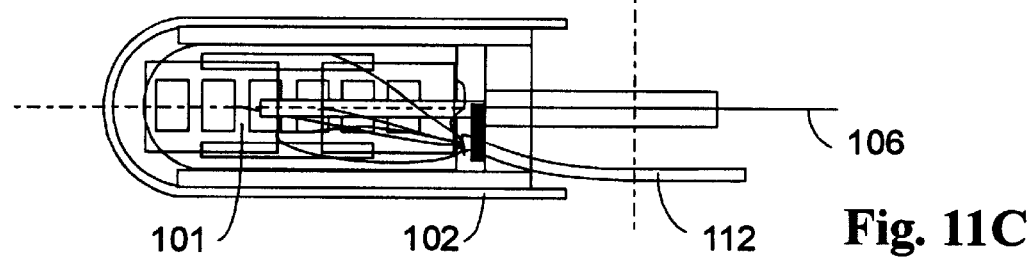
Fig. 11C
Fig. 12A
Fig. 12B
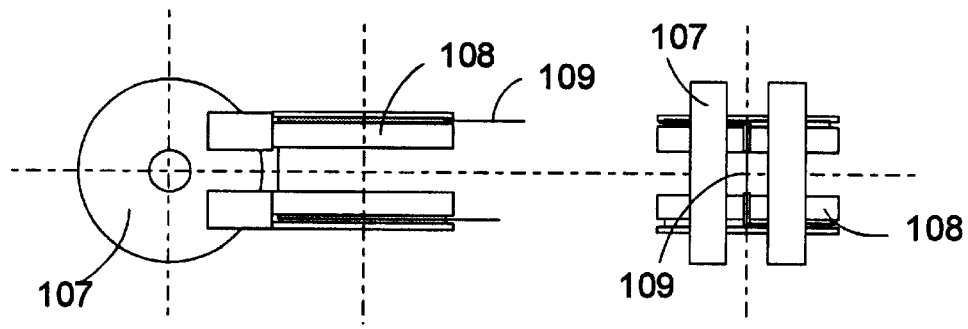
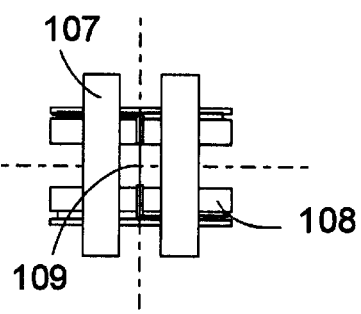
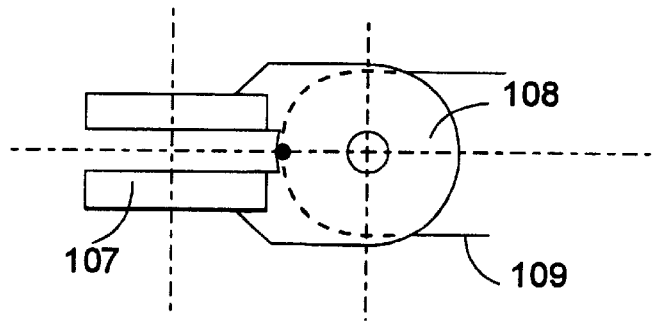
Fig. 12C

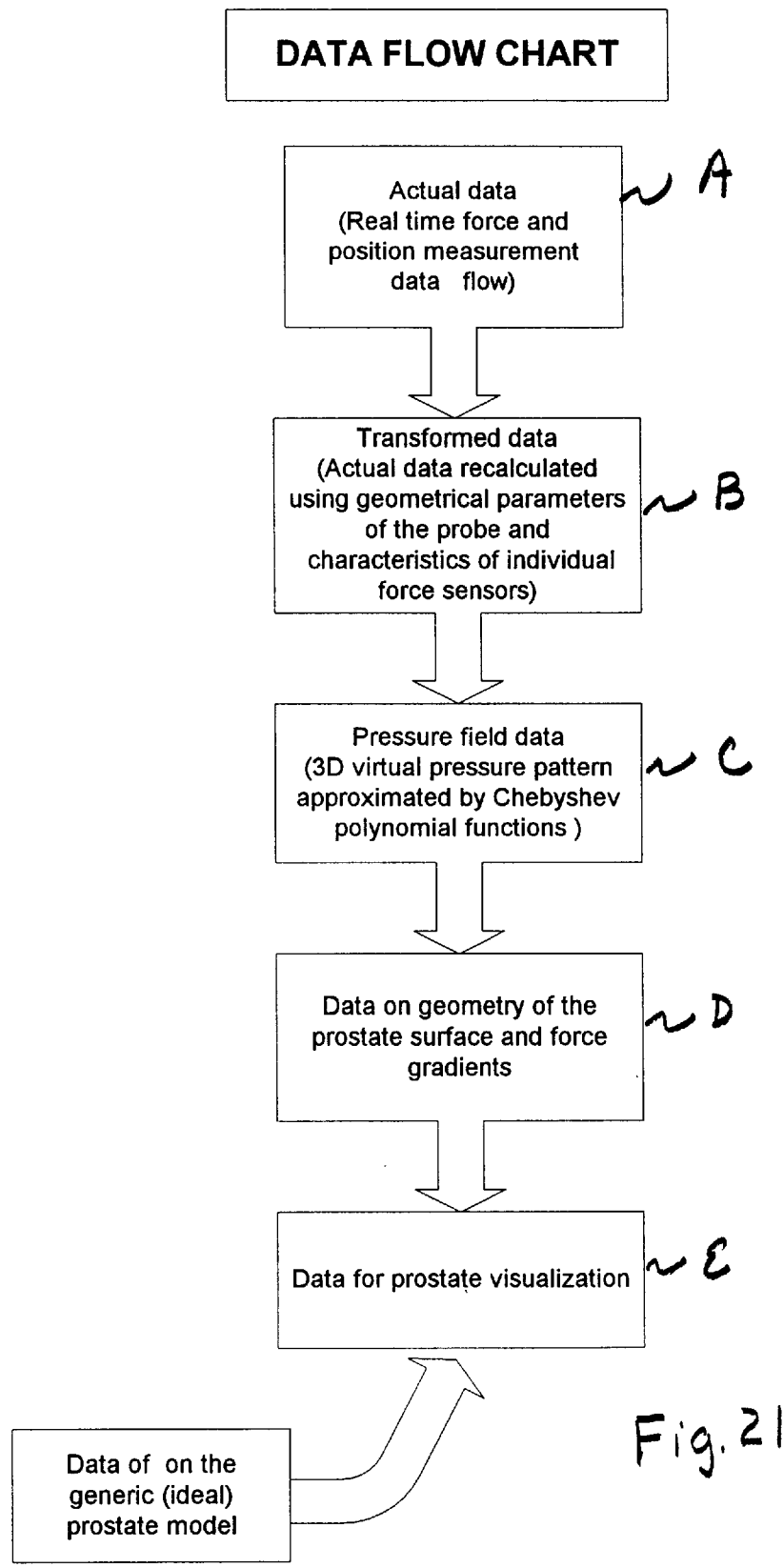

APPARATUS FOR MEASURING MECHANICAL PARAMETERS OF THE PROSTATE AND FOR IMAGING THE PROSTATE USING SUCH PARAMETERS

CROSS REFERENCE TO RELATED APPLICATION

This application is a continuation-in-part of U.S. Pat. application Ser. No. 08/607,645 filed Feb. 27, 1996 which is a continuation-in-part of U.S. Pat. application Ser. No. 07/994,109 filed Dec. 21, 1992 and issued as U.S. Pat. No. 5,524,636 on Jun. 11, 1996. The full disclosures of both applications and the issued patent are incorporated herein by reference.

BACKGROUND OF THE INVENTION

The present invention relates to apparatus for measuring geometrical and mechanical parameters of the prostate and for imaging the prostate based upon such parameters

DESCRIPTION OF THE PRIOR ART

Diagnosing early formation of tumors, particularly those caused by cancer, has been a problem that has been attempted to be solved using various techniques, such as ultrasonic imaging, nuclear magnetic resonance imaging, x-rays, and the like.

One of the safest and oldest techniques of detecting diseased tissue is palpation (digital examination). Palpation, that is, examination using the sense of touch, is based on he significant differences in elasticity of normal tissues and certain lesions. Palpation has been a commonly used technique for detecting prostate and breast cancer. Several authors have proposed various types of devices mimicking palpation to detect tumors using different types of pressure sensors. For example, Frei et al, U.S. Pat. No 4,250,894, have proposed an instrument for breast examination that uses a plurality of spaced piezoelectric strips which are pressed to the body being examined by a pressure member which applies a given periodic or steady stress to the tissue beneath the strips.

A different principle for evaluating the pattern of pressure distribution over compressed breast was proposed by Gentle (Gentle CR, *Mammobarography: -a possible method of mass breast screening.* J. Biomed. Eng. 10, 124–126, 1988). The pressure distribution is monitored optically by using the principle of frustrated total internal reflection to generate a brightness distribution. Using this technique, referred to as "mammobarography," simulated lumps in breast prostheses have been detected down to a diameter of 6 mm. According to Gentle, this technique can be used for mass breast screening; however, no quantitative data on lumps in a real breast was ever published. The failure has been explained by the insufficient sensitivity of the registration system. It should be noted, that most of the development of pressure sensors for medical applications has been done not for mimicking palpation but for monitoring blood pressure and analyzing propagation of pulse waves in blood vessels (See, for example, U.S. Pat. Nos. 4,423,738; 4,799,491; 4,802, 488; 4,860,761).

Another approach to evaluate elasticity of the tissues uses indirect means, such as conventional imaging modalities (ultrasound or MRI) which are capable of detecting motion of a tissue subjected to an external force. One approach attempts to determine the relative stiffness or elasticity of tissue by applying ultrasound imaging techniques while vibrating the tissue at low frequencies. See, e.g., K. J. Parker et al, U.S. Pat. No. 5,099,848; R. M. Lerner et al., *Sono-Elasticity: Medical Elasticity Images Derived From Ultrasound Signals in Mechanically Vibrated Targets,* Acoustical Imaging, Vol. 16, 317 (1988); T. A. Krouskop et al., *A Pulsed Doppler Ultrasonic System for Making Non-Invasive Measurement of Mechanical Properties of Soft Tissue,* 24 J. Rehab. Res. Dev. Vol. 24, 1 (1987); Y. Yamakoshi et al., *Ultrasonic Imaging of Internal Vibration of Soft Tissue Under Forced Vibration,* IEEE Transactions on Ultrasonics, Ferroelectrics, and Frequency Control, Vol. 7, No. 2, Page 45 (1990).

Another method proposed for measuring and imaging tissue elasticity is described in Ophir et al., U.S. Pat. Nos. 5,107,837, 5,293,870, 5,143,070 and 5,178,147. This method includes emitting ultrasonic waves along a path into the tissue and detecting an echo sequence resulting from the ultrasonic wave pulse. The tissue is then compressed (or alternatively decompressed from a compressed state) along the path and during such compression, a second pulse of ultrasonic waves is sent along the path into the tissue. The second echo sequence resulting from the second ultrasonic wave pulse is detected and then the differential displacement of selected echo segments of the first and second echo sequences are measured. A selected echo segment of the echo sequence, i.e., reflected RF signal, corresponds to a particular echo source within the tissue along the beam axis of the transducer. Time shifts in the echo segment are examined to measure compressibilities of the tissue regions.

Sarvazyan et al., have developed a device for elasticity imaging of the prostate using an ultrasonic transrectal probe (U.S. Pat. No. 5,265,612). This device enables physicians to quantitatively and objectively characterize elasticity moduli of prostate tissues. The elasticity characterization and imaging is achieved by evaluating the pattern of the internal strain in the prostate and surrounding tissues using conventional transrectal ultrasonography. The pattern of internal strain is obtained by ultrasonically imaging the prostate at two levels of its deformation. The deformation is provided by changing the pressure in the fluid filling the sheath surrounding the transrectal probe. In addition to elasticity, other tumor parameters reflecting the stage of its development include the geometrical parameters of the tumor, such as its volume or diameter. Lacoste et al., U.S. Pat. No. 5,178,148, have disclosed a method of determining the volume of a tumor or gland, particularly the prostate, using an endocavity detector probe, in particular, a transrectal probe.

SUMMARY OF THE INVENTION

New methods and devices for measuring geometrical and mechanical parameters of body tissues and providing mechanical imaging (MI) of the tissues based on these parameters are described in applicant's parent U.S. Pat. application Ser. No. 08/607,645 and 07/994,109. In essence, a pressure sensing array is used to measure the surface stress pattern on soft tissues, and the pattern of mechanical stress and the changes in the pattern as a function of the applied pressure, the position of the array and time are processed to construct an image of the internal structure of the tissues. The detected parameters and processed image provide sensitive information useful in the detection and diagnosis of soft tissue pathologies such and breast and prostate tumors.

In accordance with the present invention, apparatus particularly useful for mechanical imaging of the prostate comprises a transrectal probe including a probe shaft, a tip moveable in relation to the shaft, a position sensor for determining the position of the tip and an array of pressure sensors for determining the pattern of pressure from tissue deformed by the moveable tip. Signals indicaive of the position of the tip and the pattern of pressure can be provided to a processor for mechanical imaging.

In a preferred embodiment, the apparatus comprises a control handle, a probe shaft and the moveable tip. The tip is moveable in an upward and downward direction. The handle advantageously includes a control lever for controlling tip movement via a control rod and a locking mechanism for locking the tip at a predetermined position. The handle can include a switch, such as a control button, for controlling a computer. Preferably the outer surfaces of the probe are covered with a soft, thin flexible rubber sheath to permit transmission of pressure to the sensors. The probe can be composed largely of plastic materials for ease of maneuverability and biocompatibility.

BRIEF DESCRIPTION OF THE DRAWINGS

The nature, advantages and various additional features of the invention will appear more fully upon consideration of the illustrative embodiments now to be described in detail in connection with the accompanying drawings. In the drawings:

FIG. 1 is a schematic representation of a model of soft "tissue" illustrating a device for loading incorporating pressure sensors used in the present invention;

FIG. 2 is the device of FIG. 1 after loading the tissue, and illustrating a typical pressure curve across a surface of the tissue;

FIG. 3 is similar to the tissue compression in FIG. 2, illustrating the effect of a presence of a tumor in the tissue;

FIG. 4 is an illustration of the structure shown in FIG. 3, with a piston deforming tissue from a side opposite from the pressure plate;

FIGS. 11A–C are detail views of the probe tip showing a pressure sensor array and a position/orientation sensor;

FIGS. 12A–C are detail views of the probe joint which permits articulation of the probe tip;

FIG. 21 is a chart showing the flow of data in the preferred imaging process.

Figure 5:
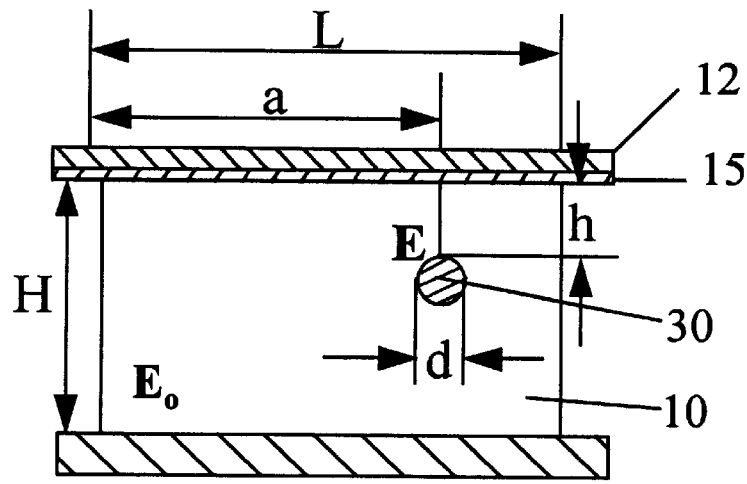
FIG. 5 is a schematic illustration of loading parameters for a model tissue being examined and a tumor in such tissue; differential pressure ratio.

It is to be understood that the drawings are for purposes of illustrating the concepts of the invention and, except for the graphs, are not to scale.

DETAILED DESCRIPTION OF THE INVENTION

This disclosure is divided into two parts. Part I describes several embodiments of the transrectal probes particularly useful for measuring geometrical and mechanical parameters of the prostate, and Part II describes the use of the probe and the parameters it acquires to provide a mechanical image of the prostate.

I. Probes For Measuring Geometrical and Mechanical Parameters of the Prostate Referring to the drawings, FIGS. 15A–D illustrate a preferred embodiment of a transrectal probe for measuring geometrical and mechanical parameters of the prostate. In essence, the probe 300 comprises a control handle 307, such as a pistol grip handle, a probe shaft 306, such as a rigid tube, extending along an axis from the handle, and a moveable tip 301 including an array of pressure sensors 302 on the tip surface 303 and a position/orientation sensor 304 for measuring the position of tip 301. The tip is moveable above and below the axis of the shaft. In its axial position, the tip can measure pressure from surfaces of the prostate parallel to the axis. When tilted above the axis, the tip can measure pressure from rising surfaces of the prostate, and when tilted below the axis, it can measure falling surfaces of the gland.

Moveable tip 301 is coupled at axis 305 to rigid tube 306. Rigid tube 306 is attached to pistol grip handle 307. Rigid rod 308 is positioned within rigid tube 306. End 309 of rigid rod 308 is coupled to moveable tip 301 and end 310 of rigid rod 308 is coupled to probe tip control lever 311. Probe tip control lever 311 can be depressed and released for moving moveable tip 301 by rigid rod 308 in an upward vertical direction 312 or in a downward vertical direction 313, allowing moveable tip 301 to be articulated over angles in the range of ±45.

Lever button 314 can lock the tip angle. End 315 of lever 311 is attached to end 310 of rigid rod 308. Locking rod 317 is formed on lever button 314. Releasing the lever button 314 positions end 318 of locking rod 317 in one of a plurality of depressions 319 formed in pistol grip handle 307, thereby locking moveable tip 301 at a predetermined position. Thereafter, lever button 314 can be depressed again to release moveable tip 301.

The position/orientation sensor can be a 3SPACE® Inside Trak™ sensing element made by Pohlemus Inc. It will be appreciated that other position sensors known in the art can also be used.

Switch 320 is used for controlling interactions with computer interface 322. Switch 320 is positioned within pistol grip handle 307. Control button 321 is coupled to switch 320. Control button 321 can be depressed at various stages during use for controlling input from pressure sensor 302 and position orientation sensor 304 to computer interface 322 through cable 323. For example, control button 321 can be depressed at the beginning and end of an examination session.

Figure 15A:
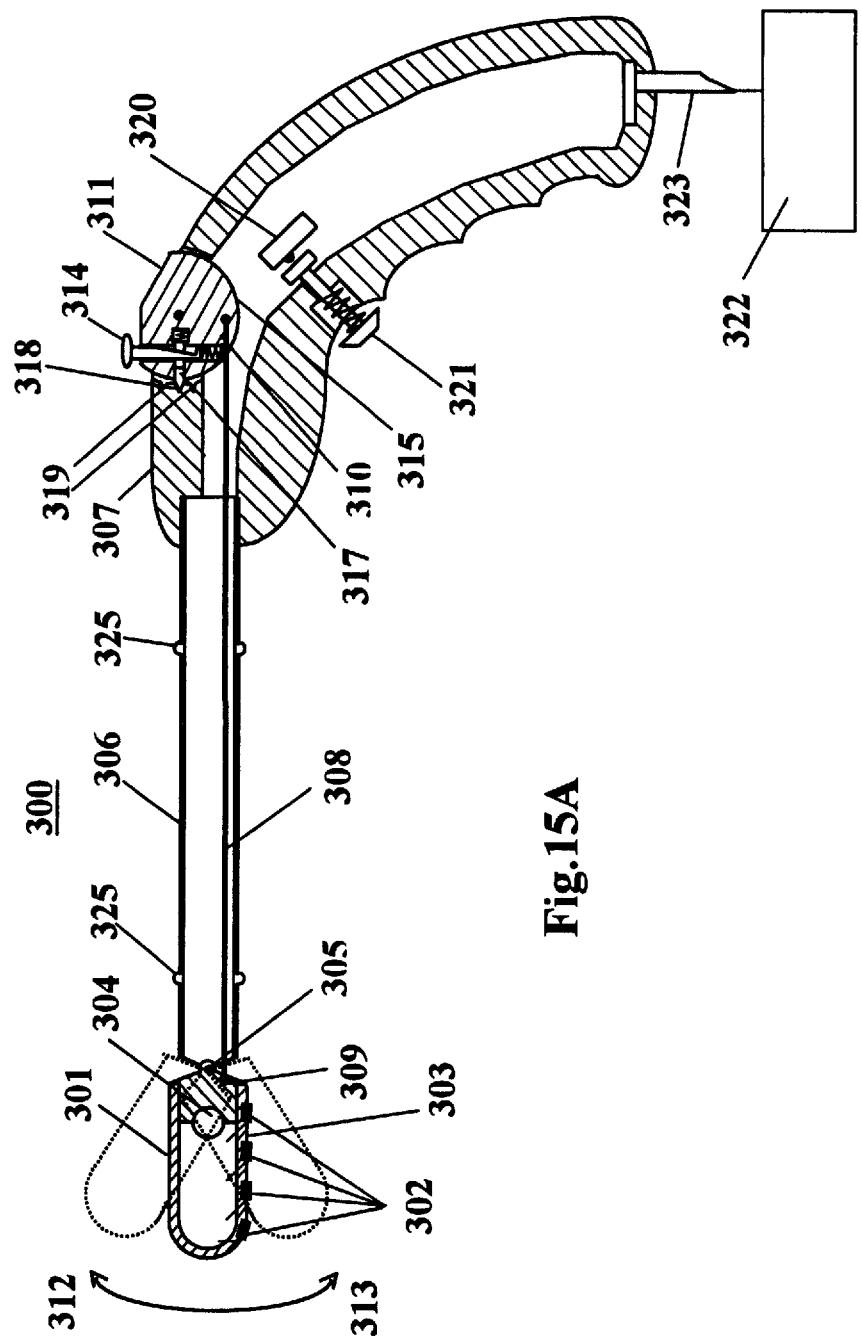
FIG. 15A is a side sectional view of an alternate embodiment of a transrectal probe in accordance with the teachings of the present invention.
Figure 15B:
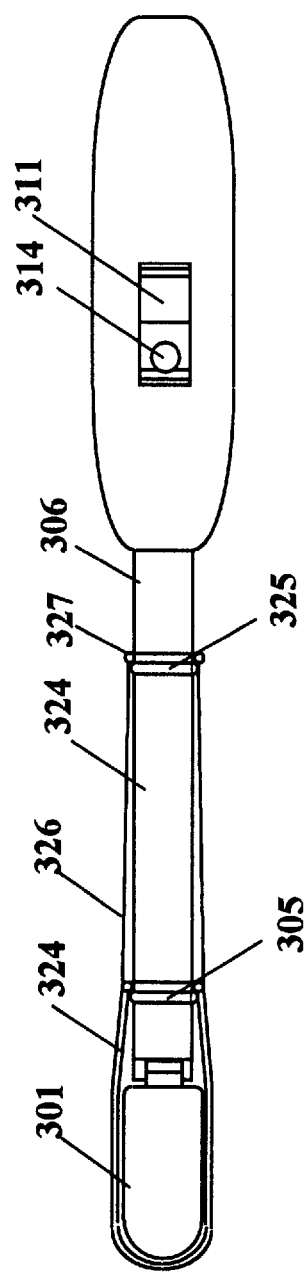
FIG. 15B is a top view of the transrectal probe shown in FIG. 15A including a sheath.

Sheath 324 covers a portion of rigid tube 306 and moveable tip 301 for preventing damage to moveable tip 301, as shown in FIG. 15B. Sheath slippage guard ribs 325 can be positioned along rigid tube 306. Sheath 324 is held by sheath slippage guard ribs 325 to rigid tube 306. Preferably, sheath 324 is formed of a latex material. Disposable sheath 326 can be placed over sheath 324 to cover entire moveable tip 301. For example, disposable sheath 326 can be a conventional condom. Disposable sheath 326 can be retained on rigid tube 306 with rubber ring 327.

Figure 15C:
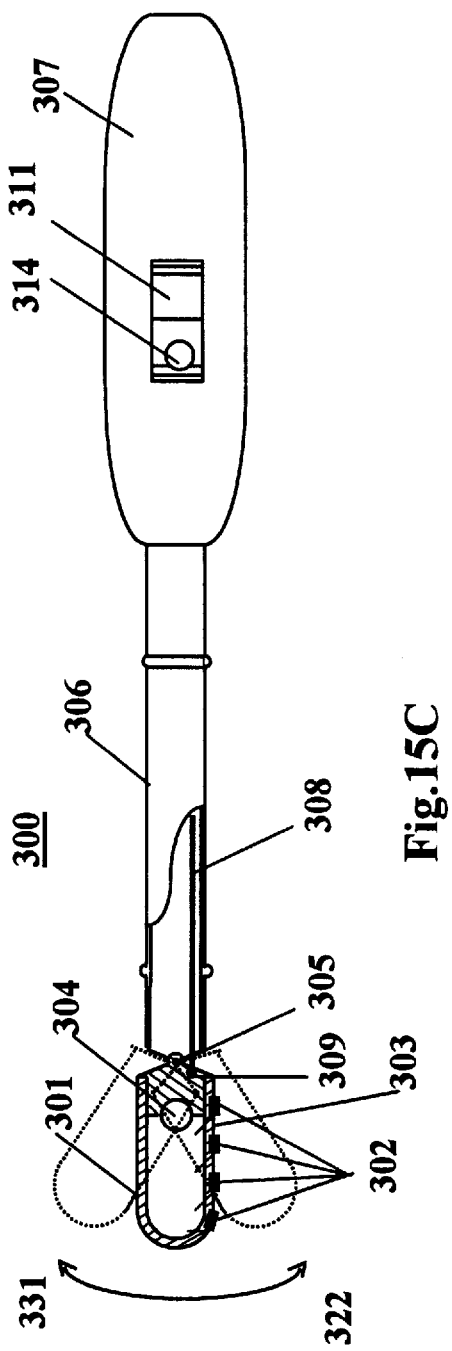
FIG. 15C is a top view of the transrectal probe shown in FIG. 15A for use by a right-handed user.
Figure 15D:
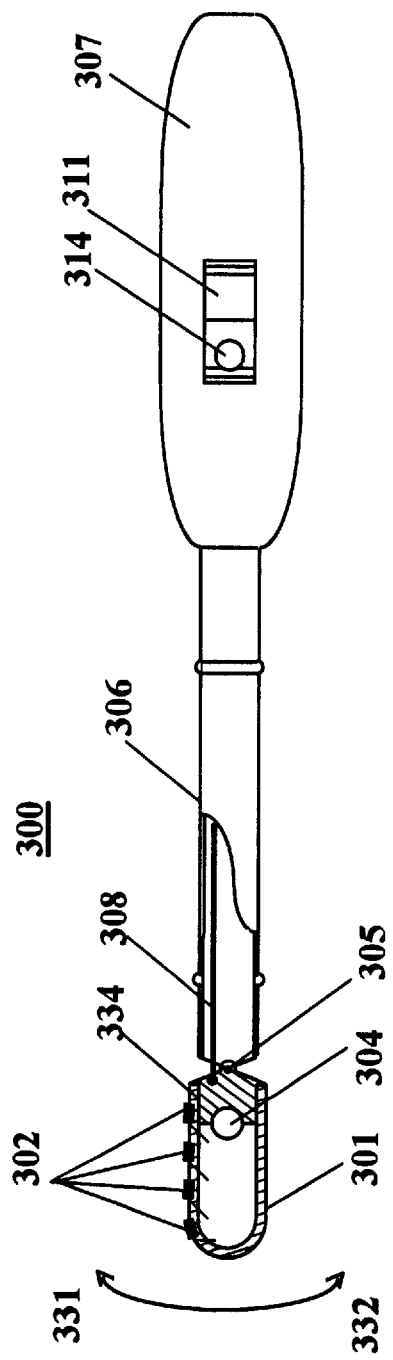
FIG. 15D is a top of the transrectal probe for use by a left-handed user.

FIG. 15C illustrates a top view of probe 300 for transrectal mechanical imaging by a right-handed user of probe 300 with horizontal movement in the direction of arrows 331 and 332. Pressure sensors 302 are positioned on left surface 303 of moveable tip 301 for simulating the movement of a finger tip of a right-handed user of probe 300. FIG. 15D illustrates a top view of an embodiment of probe 300 for transrectal mechanical imaging by a left-handed user of probe 300. Pressure sensors 302 are positioned on right surface 334 of moveable tip 301 for simulating the movement of a finger tip of a left-handed user of probe 300.

Probe 300 can be used for examination of the prostate in two different positions. In the first position, the patient to be examined is in a kneeling position with their face in a downward position. The prostate is positioned below probe 300. In the second position, the patient to be examined is in a jackknife position laying on their side. When the patient is laying on their right side, the prostate is positioned on the left side of the patient's rectum. In this position, the embodiment of the probe shown in FIG. 15C for a right-handed person is used for examination. When the patient is laying on their left side, the prostate is positioned on the right side of the patient's rectum. In this position, the embodiment of the probe shown in FIG. 15D is used for examination.

Preferably, rigid tube 306, moveable tip 301 and pistol grip handle 307 are formed from plastic FDA grade acetal polymer for biocompatibility. The use of a plastic material also has the advantage of non-interference with position/ orientation sensors that can be magnetic field sensitive. It will be appreciated that rigid tube 306, moveable tip 301 and pistol grip handle 307 can also be formed of aluminum and other conventional light-weight metals. Probe 300 has the advantage of manually controlling a moveable sensing tip without motors or electricity. Probe 300 is formed of a light-weight material for ease in manipulation of the probe. Probe 300 can be used in a similar manner as probe 100 described above for mechanical imaging and detecting tumors in the human prostate gland.

Figure 16A:
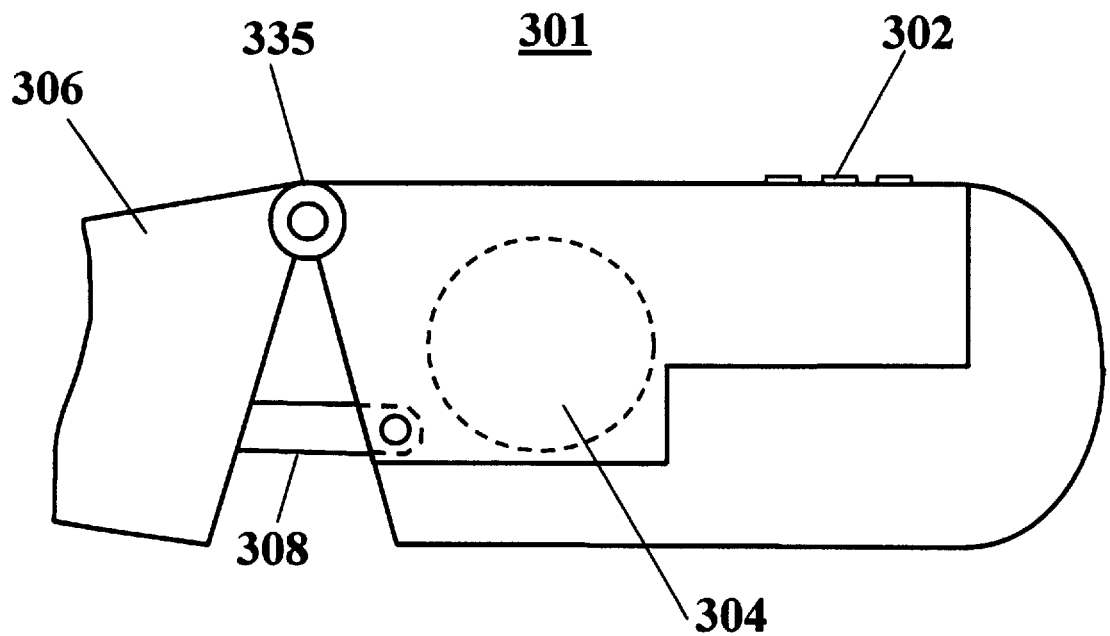
FIG. 16A and 16B are side and bottom views of a preferred moveable tip for the probe of FIG. 15A.
Figure 16B:
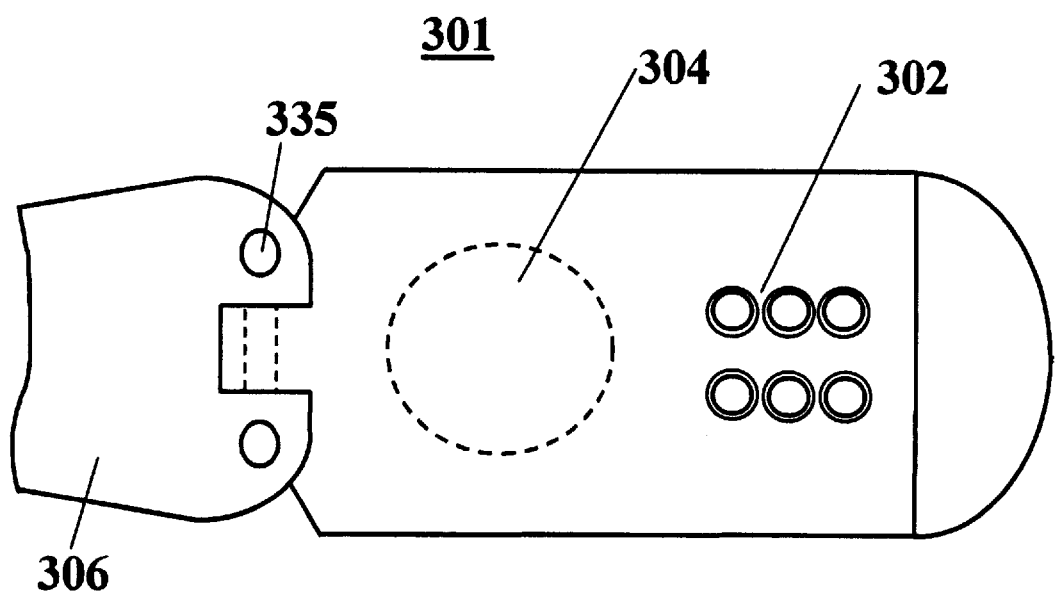

FIGS. 16A and 16B are enlarged side and bottom views, respectively of the preferred moveable tip 301 showing advantageous locations of the array of pressure sensors 302 and position/orientation sensor 304. The tip 301 is connected to the shaft 306 by a hinge 335. Extension of rod 308 can thus move the tip 301 below the shaft axis (in the direction of the sensors) and retraction can move the tip in the opposite direction above the shaft axis.

Preferably, the array of pressure sensors are arranged in a left row 302*a* and a right row 302*b*. Left row 302*a* measures pressure applied against the left side of tip 301 and right row 302*b* measures pressure applied against the right side of tip 301. Left row 302*a* and right row 302*b* provide feedback to the user of probe 300 to assist in controlling positioning of probe 300 within the patient. For example, probe 300 can be manipulated within the patient to be examined in order to provide equal pressure at left row 302*a* and right row 302*b*, thereby determining the correct position of probe 300 and aiding the user in performing the examination procedure.

Figure 17:
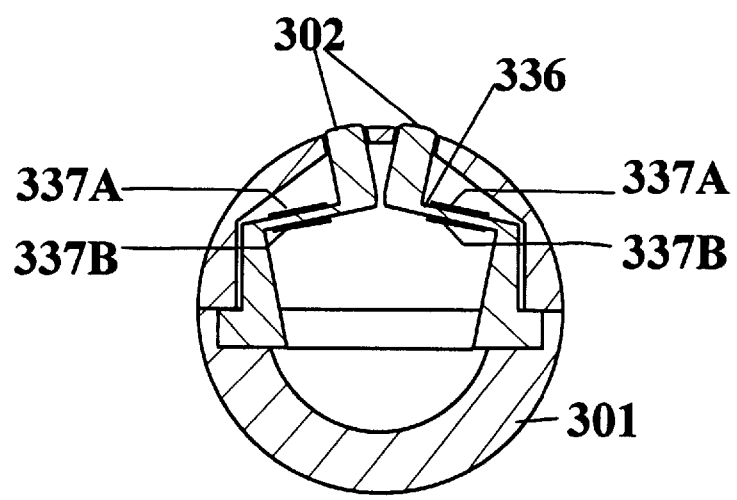
FIG. 17 is a cross section of the tip of FIG. 16A, showing a preferred sensor arrangement.

FIG. 17 is a cross section of moveable tip 301 through a pair of pressure sensors 302 illustrating the preferred pressure sensors which are advantageously bending beam force sensors. Force applied to sensor region 302 bends beam portion 336 which is detected by a pair of strain gauges 337A, 337B bonded on opposite sides of each beam 336. The tip walls, sensor regions 302 and beam portions 336 are all preferably plastic.

Figure 18:
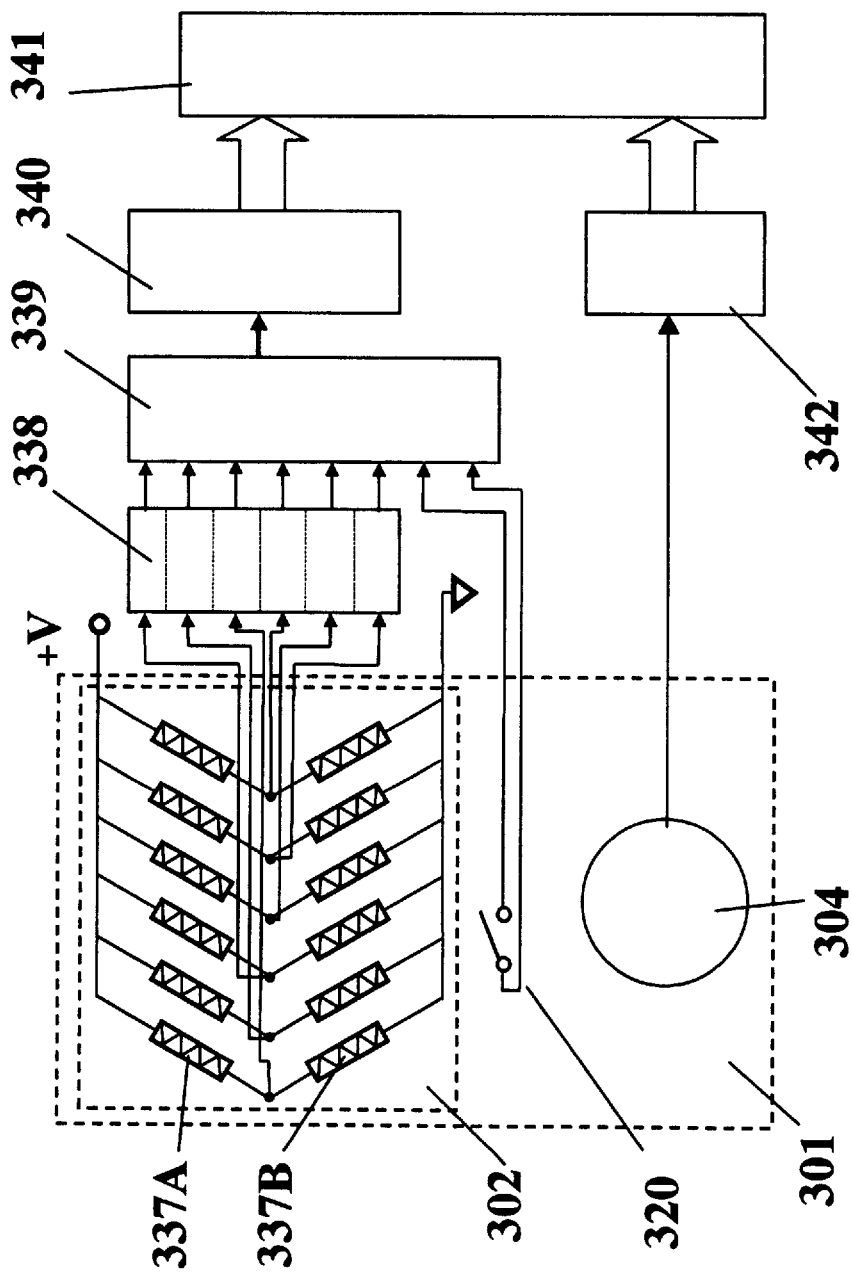
FIG. 18 is a schematic circuit diagram showing the signal paths from the probe sensors.

FIG. 18 is a schematic circuit diagram showing the original paths from the probe sensors to the signal processing circuitry. Signals from each strain gauges 337A and 337B pass first to a preamplifier, here a six-channel preamplifier, 338. The amplified signals are applied to a multiplexer 339, and the multiplexer signals are converted to digital signals by A/D converter 340 and fed into computer 341 for signal processing. The signal from probe switch 320 can be conveniently provided to the computer via multiplexer 339. The signals from position/orientation sensor 304 are detected by the associated interface circuitry 342 and provided directly to the computer.

II. Use of the Probe In Mechanical Imaging of the Prostate

The method for transrectal imaging of the prostate using the present invention is based on a new technology of medical imaging described in U.S. Pat. No. 5,524,636, which is incorporated herein by reference. This method is referred to herein as Mechanical Imaging ("MI"). The essence of MI is the reconstruction of the internal structure of soft body tissues by measuring a surface stress pattern using a pressure sensing array. The pattern of mechanical stress and its changes as a function of applied pressure and time contain comprehensive information on the mechanical properties and geometry of the internal structures of the body tissues.

The most promising applications of MI devices are in those fields of medicine where palpation is proven to be a sensitive tool in detecting and monitoring diseases, including prostate cancer. Palpation, i.e. digital rectal examination (DRE), is currently the most common method of prostate cancer detection. Despite the obvious usefulness of the diagnostic information obtained by DRE, there are no technical means and devices capable of yielding data similar to that obtained by the finger of a skilled examiner. To examine the gland, a physician inserts a finger into the rectum and, feeling the gland through the rectal wall, searches for abnormalities in its size, contour, consistency and localization. A hard, nodular, or indurated prostate discovered on routine DRE may be the first indication of cancer.

The probe in accordance with the present invention in inserted into the rectum and manipulated using the handle. The tip applies pressure similar to that applied by a human finger. The pressure sensors mounted on the tip measure the localized pressure distribution. The position/orientation sensor provided in the tip determines the position of the tip corresponding to the particular pressure pattern measured by the pressure sensor array. Signals from the pressure sensor array and position/orientation sensor are used to calculate a virtual pattern of a property such as stress and strain for the examined prostate. A theoretical geometrical model of the examined prostate is defined assuming that the tissue is homogeneous and has dimensions estimated from the measurement data. Theoretical patterns of stress and strain are then evaluated using said theoretical geometrical model. The virtual pattern and theoretical pattern of strain or stress are compared and differences indicate location and relative hardness of a differing elasticity region. The theoretical geometrical model is then adjusted by varying the spatial distribution of elasticity to minimize the differences. This adjustment of the geometrical and mechanical parameters of model is iteratively repeated until said differences become less than a preselected level. Thus, an inverse mechanical problem is solved and a spatial distribution of elasticity modulus is obtained in the tissue portion being examined. The resultant distribution is used to construct and display an image of the examined prostate.

Without being bound by any particular posited theory, the following constitutes applicant's belief concerning the theoretical aspects of the invention. The pressure patterns on the surface of an investigated tissue portion together with given boundary conditions enable one to reconstruct internal structures in underlying tissue and to evaluate relative hardness and softness of tissue in localized areas. The relationship between elasticity differences in localized areas inside of tissue, the stress pattern on the surface of the tissue, and internal strain pattern permit detecting and quantifying tissue abnormalities.

When calculating the mechanical properties of tissues, calculations are based on a model of the tissue as being linearly elastic and incompressible media. Such an approach is a first approximation which is sufficient to solve all questions arising in mechanical elasticity imaging.

Accordingly, the graphical representations discussed in the detailed description of the invention are based on calculations from the general equations presented below. The following equations are general equations for three-dimensional linear theory of elasticity for in-compressible media like tissues or another water based system, that is a system having a Poisson s ratio of 0.5 (Sarvazyan et al., Biophysical Bases of Elasticity Imaging, Acoustical Imaging, Vol. 21, 223, 1995).

The equations for dynamic equilibrium are:

$$\frac{\partial \sigma_{xx}}{\partial x} + \frac{\partial \sigma_{xy}}{\partial y} + \frac{\partial \sigma_{xz}}{\partial z} = \rho \frac{\partial^2 U}{\partial t^2} \quad (1)$$

$$\frac{\partial \sigma_{xy}}{\partial x} + \frac{\partial \sigma_{yy}}{\partial y} + \frac{\partial \sigma_{yz}}{\partial z} = \rho \frac{\partial^2 V}{\partial t^2}$$

$$\frac{\partial \sigma_{xz}}{\partial x} + \frac{\partial \sigma_{yz}}{\partial y} + \frac{\partial \sigma_{zz}}{\partial z} = \rho \frac{\partial^2 W}{\partial t^2}$$

where:
U, V, W are components of displacement;
$\rho$ is density of media; and
$\sigma_{ij}$ are components of stress tensor.

The pattern of stresses must be related to a pattern of strain. This relationship for incompressible media (e.g. tissues or other water based systems) is given by the following equations.

$$\sigma_{xx} = P + 2\mu E_{xx} \quad \sigma_{yy} = P + 2\mu E_{yy} \quad \sigma_{xx} = P + 2E_{zz} \quad (2)$$
$$\sigma_{xy} = 2\mu E_{xy} \quad \sigma_{xz} = 2\mu E_{xv} \quad \sigma_{yz} = 2\mu E_{yz}$$

where $$\mu = \frac{E}{2(1+v)},$$

where v=0.5 is the Poisson ratio, E is the Young's Modulus and $$E_{xx} = \frac{\partial U}{\partial x}, E_{yy} = \frac{\partial V}{\partial y}, E_{zz} = \frac{\partial W}{\partial z},$$

$$E_{xy} = \frac{1}{2}\left(\frac{\partial U}{\partial y} + \frac{\partial V}{\partial x}\right), E_{xz} = \frac{1}{2}\left(\frac{\partial U}{\partial x} + \frac{\partial W}{\partial z}\right),$$

$$E_{yz} = \frac{1}{2}\left(\frac{\partial V}{\partial z} + \frac{\partial W}{\partial y}\right).$$

By combining equations (1) and (2), we can obtain three equations containing only three unknowns, U, V, W, which are components of displacement plus the unknown pressure P.

An additional equation is the equation of incompressibility showing that divergence of vector of displacement equals zero:

$$\frac{\partial U}{\partial x} + \frac{\partial V}{\partial y} + \frac{\partial W}{\partial z} = E_{xx} + E_{yy} + E_{zz} = 0 \quad (3)$$

Equation (3) represents the condition that when force is applied to the soft tissue, all the deformation of tissue is related to changes of the shape of the soft tissue but not the volume, because Poison s ratio is 0.5, that is the bulk compressional modulus of soft biological tissues is many orders of magnitude higher then the shear elasticity modulus.

The mechanical characteristics of tissue involve not only elasticity as discussed, but also viscosity. Thus, the tissue is a viscoelastic material that requires description in both viscous and elastic components. Viscosity affects the information received because with a viscoelastic material, there is a time delay between force application and any displacement that occurs. In a dynamic mode where force is applied in time, the development of stresses in time provides the information on viscosity.

In case of viscoelastic media, the components of the stress tensor in equation (2) should have following additional terms for shear viscosity, $\mu^*$ $$2\mu^* \frac{\partial E_{ij}}{\partial t}$$

The shear modulus and Young's modulus of soft tissue are different by a factor of 3, because Poisson s ratio is 0.5. While either modulus can be used for examination of the tissue, Young's modulus is used in the description of the present invention.

In the case of harmonic disturbances, temporal dependence can be easily removed from these equations and the system of the differential equations for amplitudes will be obtained.

FIG. 1 illustrates a portion of a soft tissue 10 that is supported on a base 11 which supports a flat rigid plate 12 capable of exerting pressure thereon from a force generator 13. A series of individual pressure sensors indicated at 15 are provided on the bottom surface of the plate 12 to sense pressure in an array across the surface of tissue 10.

FIG. 2 represents a pressure profile P(x) of the homogeneous tissue 10 when deformed. FIG. 3 illustrates a homogeneous tissue pressure profile in the dotted line and the profile of tissue 10 having an inclusion 18 in the solid line. The difference between these two pressure profiles shown in FIG. 3 provides information on the presence, location, and relative elasticity of inclusion 18 with respect to surrounding tissue 10. The strain pattern on the surface of the tissue 10 as shown in FIG. 3 is in this case represented in the form of pressure profile P(x). This strain pattern depends on the presence of an inclusion 18, as well as on the dimension of the tissue 10, neighboring anatomical features of that tissue, such as presence of a bone, and on the geometrical relationship of the tissue 10, support member 11 and deformation member 12. Therefore, the difference between the measured profile P(x) and the profile $P_o(x)$, shown by the dotted line, theoretically calculated for a homogenous model of that tissue under same boundary conditions, contains direct information on the inclusion, rather than the strain profile P(x) itself.

FIG. 4 schematically illustrates how the present invention enhances the amplitude of the pressure profile and, thus, improves detection of an inclusion. In this instance, the tissue 10 is supported on a base 11, and a schematically shown piston or block 24 which also is called a "finger" as used in palpation, is provided on the base and is caused to protrude into the tissue and compress the tissue in a localized area indicated at 26 directly below inclusion 18, which can be a tumor.

The represented pressure profile schematically disposed on the top of the pressure plate 12 (which is displaced the same as that previously explained) represents the data provided by the pressure sensors 15. P(x) is represented as a dashed line and is the profile substantially as that shown in FIG. 3. P*(x), indicated by line 28, represents the pressure profile resulting from the presence of the piston 24 directly under the tumor. The piston 24 acts like a probe to cause extra compression in the desired region (e.g., inclusion 18) in addition to the general compression of the tissue 10 between plate 12 and base 11. This results in a substantial increase in the pressure profile P*(x) which reaches a maximum at $P^*_{max}$ directly over the tumor. By comparing the respective pressure profiles P(x) and P*(x), one can recognize that a much greater amplitude of the pressure profile can be obtained from the pressure sensors (to indicate an abnormality) when a probe (e.g., piston 24) or other extra compressive force is directed in the region of a tumor. In this case, a change in the pressure profile amplitude because of the piston 24 is represented as $\Delta P^* = P^* - P$.

FIGS. 5–9 are schematic examples to illustrate the applicability of the theory to the methods and devices disclosed, and to show the range of variables and measured parameters available for calculating meaningful values for quantitative analysis and evaluation. The illustrations of tissue are not meant to represent any particular portion of a human body.

Figure 5A:
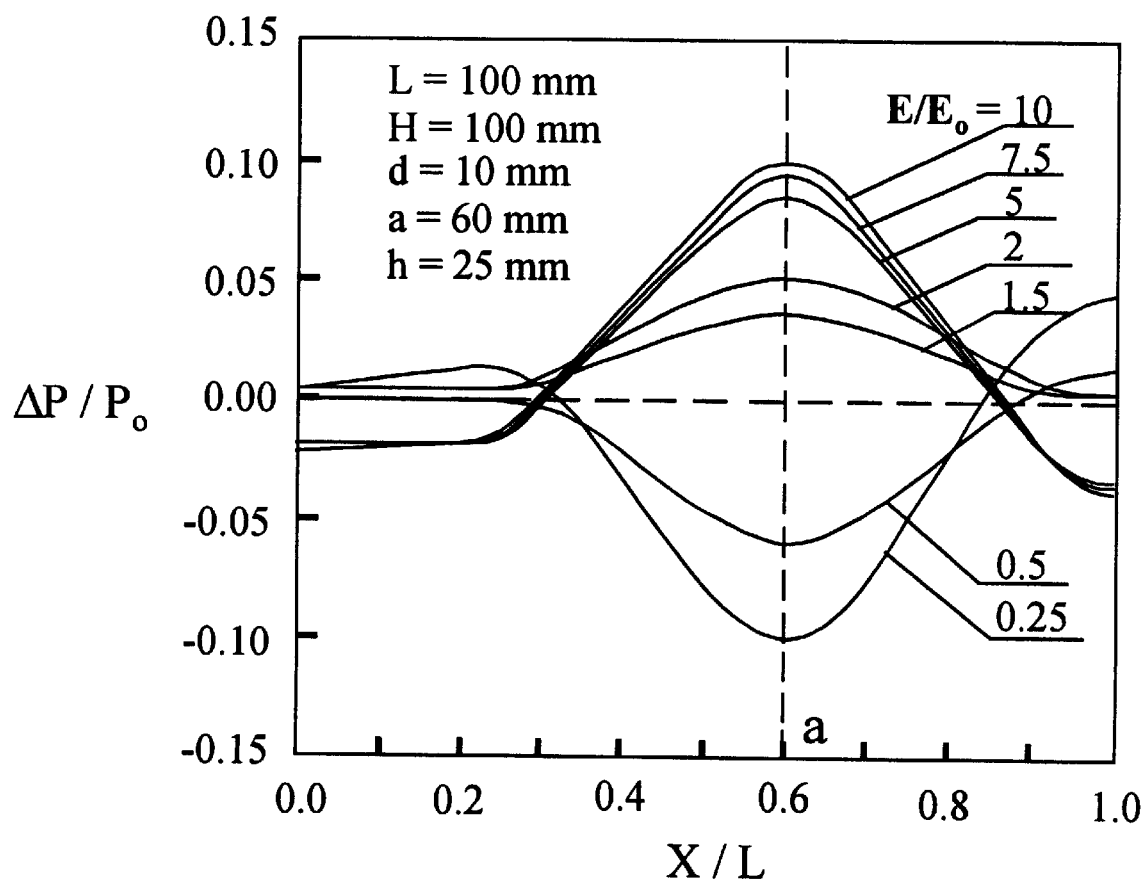
FIG. 5A is a plot of calculated differential pressure ratio across the surface at differing ratios of moduli of elasticity ratio between surrounding tissue and a tumor.

In FIG. 5, a schematic representation illustrates tissue having a tumor therein of a certain size and location. The graph of FIG. 5A illustrates a particular calculated differential pressure ratio as a function of the distance along the horizontal axis on the surface of the tissue. The graph is based on the dimensions shown in FIG. 5 having certain values, such as those listed in FIG. 5A. The symbol (E) represents the elasticity modulus (Young's modulus) of the tumor and ($E_o$) represents the elasticity modulus (Young's modulus) of the surrounding tissue. A ratio of these two moduli of elasticity ($E/E_o$) provides an indication of the hardness of the tumor relative to the surrounding tissue.

It is known that the Young s or shear elasticity modulus of a tumor varies significantly from the modulus of elasticity for surrounding tissue. For example, carcinoma may have an elasticity modulus of 10 times the elasticity modulus of normal tissue. However, in some cases, the elasticity modulus of tumors may not be substantially different from that of normal tissue making the tumors "nonpalpable". FIGS. 5 and 5A illustrate that the differential pressure profile ratio, namely ($\Delta P/P_o$), (a change in amplitude of the pressure sensed at an inclusion divided by the pressure in that region of normal tissue) in the region surrounding the tumor is quite sensitive to changes in the elasticity modulus ratio ($E/E_o$).

In FIG. 5, a "block" of tissue 10 has a height H from a base to the contact point with the pressure sensors 15, and has a length L extending along the "X" direction (i.e., horizontal axis). A tumor 30 is positioned in the tissue 10, and is located a distance below the loading plate 12 equal to (h) and it has a diameter (d). Tumor 30 is located along the horizontal axis at a distance (a) from a left edge of the tissue 10.

FIG. 5A is a graph illustrating the differential pressure ratio ($\Delta P/P_o$) (values shown on the vertical axis), as a function of the distance along the X axis from the left edge of the tissue 10 to the right. The position of the tumor 30 at (a) is indicated by a vertical dotted line in FIG. 5A. Several plots of ($\Delta P/P_o$) as a function of (X/L) are shown, each corresponding to a given ratio of moduli of elasticity ($E/E_o$), which indicates the relative hardness between a tumor and normal tissue.

With the parameters having the values shown in FIG. 5A, the plots illustrate that a tumor/tissue combination having an elasticity moduli ratio ($E/E_o$) of only 1.5, i.e., the tumor having a modulus of elasticity of 1.5 times that of the surrounding tissue, a detectable change in the pressure signal of about 3% is observed for the region surrounding the tumor. This means that even tumors that are not much harder than surrounding tissue can be detected quite easily. It is known that a tumor in a breast, for example, can be detected by a palpation (which is the only technique available for evaluating elasticity), but palpation is reliable only when the tumor has progressed so its Young's modulus is more than five to ten times larger than that of surrounding tissue. The differential pressure signal ($\Delta P/P_o$) shows a more pronounced effect near the tumor when the elasticity moduli ratio ($E/E_o$) is 2 or 5 or more. However, in this case when the elasticity moduli ratio is greater than 7.5 (e.g., 10), there is not a substantial increase in the differential pressure profile above that shown for $E/E_o=7.5$.

When tumors or inclusions are softer than the surrounding tissue, e.g., the ratio ($E/E_o$) is 0.5, a substantial difference in the differential pressure profile ($\Delta P/P_o$) in the region of the tumor is readily observable. A more pronounced effect occurs when the ratio ($E/E_o$) is 0.25. Accordingly, by observing a relatively small change in the pressure profile (only 2–10%), one can detect tumors that have a relatively small change in the modulus of elasticity. This clinically significant data is obtained by using a pressure sensor array extending across the surface of the tissue and external to the tissue that measures a pressure profile response during compression of the tissue.

Figure 6:
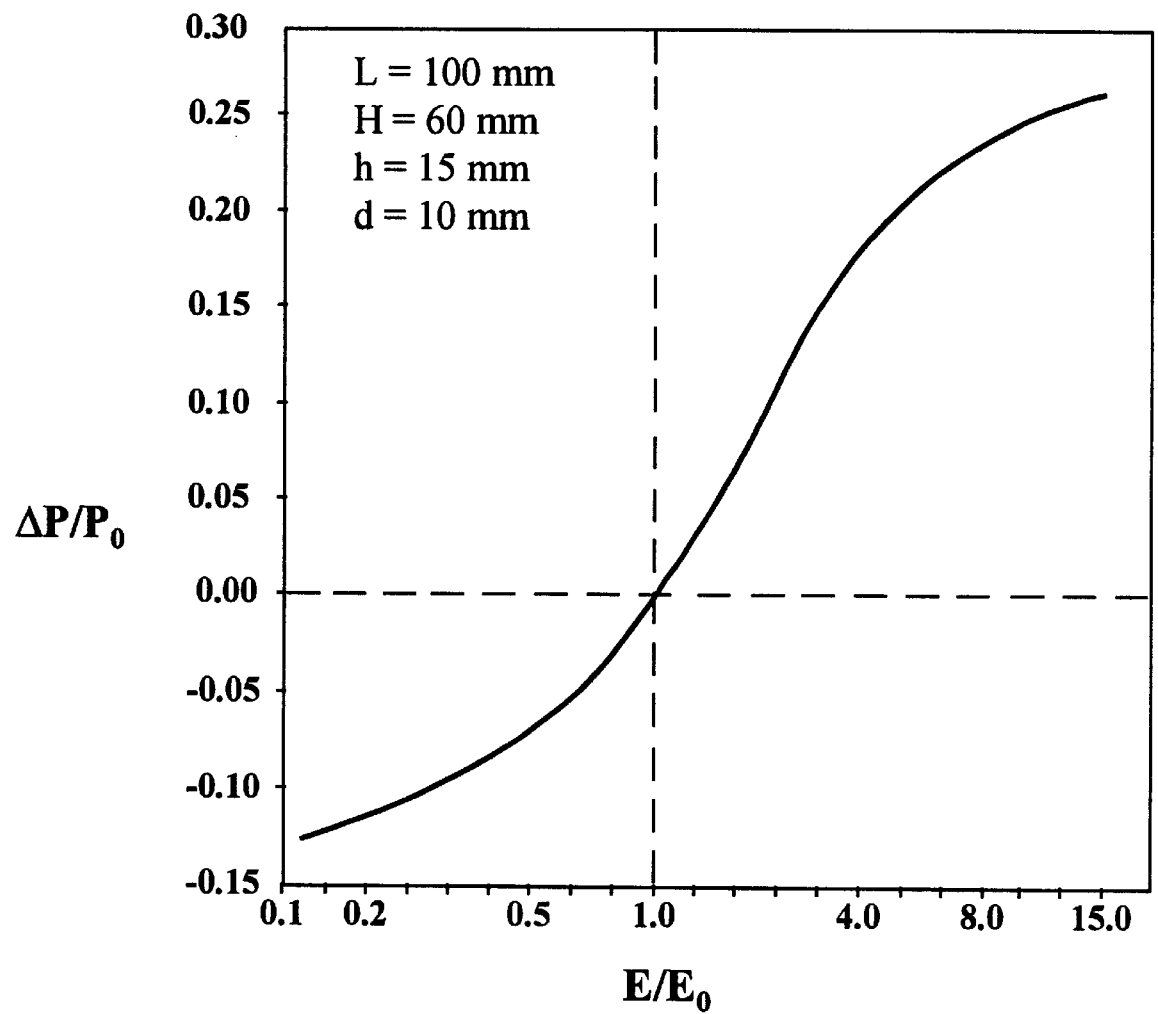
FIG. 6 is a graphical representation of the calculated relationship between differential pressure ratio and moduli of elasticity ratios for a loading structure shown in FIG. 5.

FIG. 6 illustrates the changes in pressure sensed as a function of the change in the elasticity modulus ratio ($E/E_o$).

Similar to the illustration in FIGS. 5 and 5A, FIG. 6 shows that easily achievable resolution of a few percent in the pressure profile ratio ($\Delta P/P_o$) can enable one to detect inclusions differing from the surrounding tissue in hardness to an extent which does not permit palpatory detection. The graph is based on a tissue block 10 having the parameters such as indicated on FIG. 6. The values on the horizontal axis ($E/E_o$) are provided on a logarithmic basis to facilitate comparison purposes.

Figure 7:
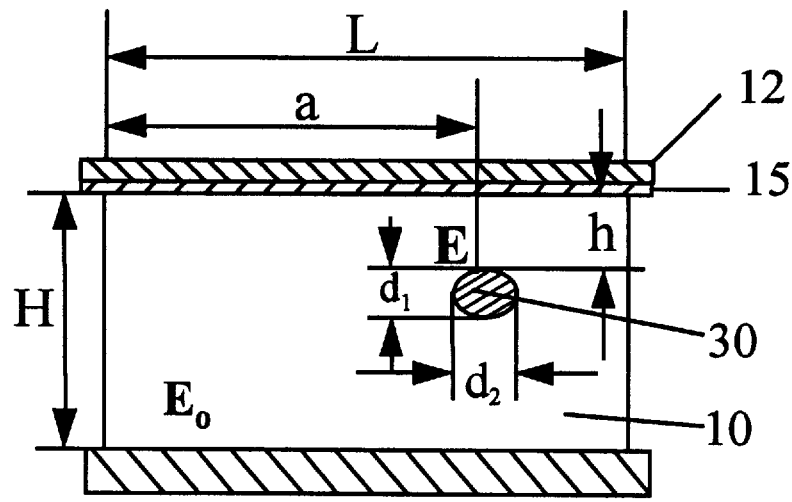
FIG. 7 is a schematic representation similar to that shown in FIG. 5 with certain loading parameters illustrated.
Figure 7A:
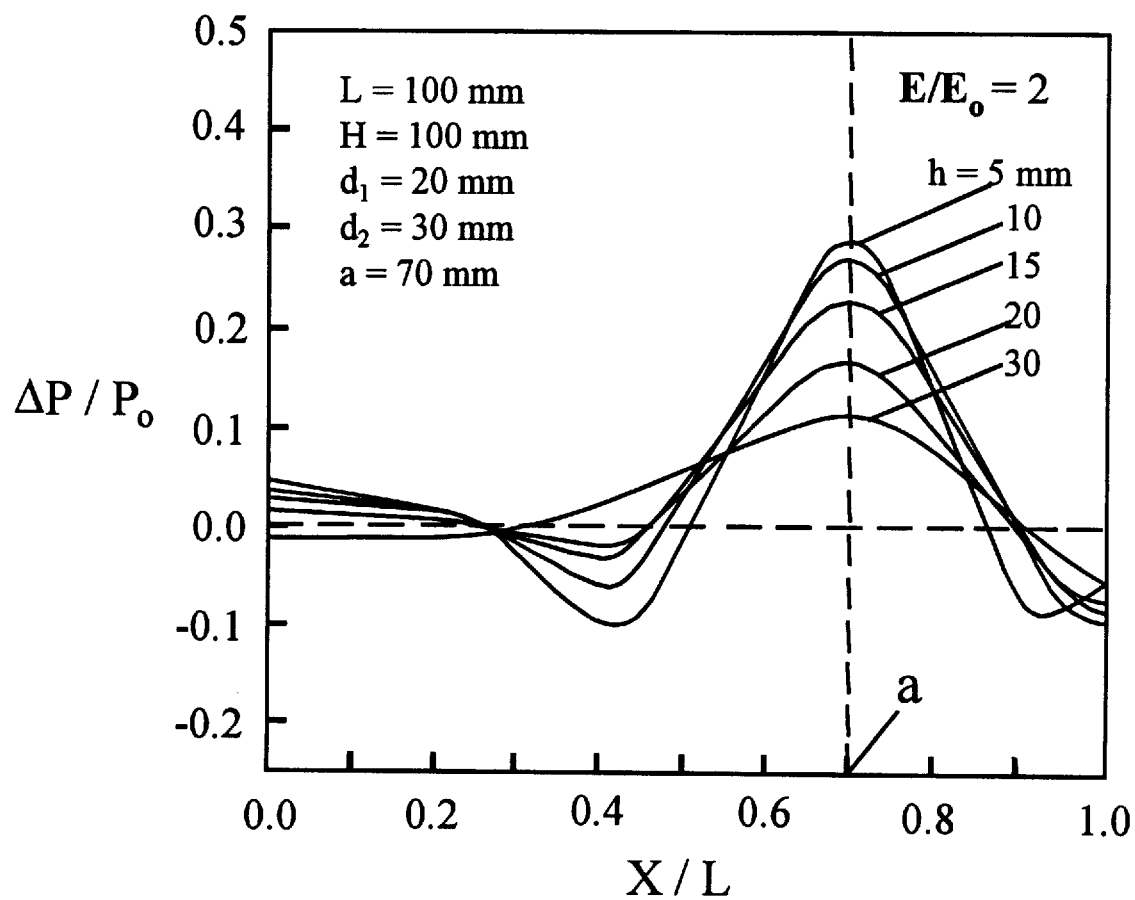
FIG. 7A is a graphical representation of the calculated differential pressure ratio across the surface at differing depths of a tumor in tissue shown at FIG. 7.

FIGS. 7 and 7A illustrate that the capability to detect a tumor within a block of tissue depends on the distance of the tumor from the tissue surface (skin) and pressure sensors. As seen in FIG. 7, the block of tissue 10 has a tumor 30 located therein and, in this instance, the vertical height of the tumor is represented as $d_1$ and the lateral width of tumor is represented as $d_2$. The parameter (a) represents the tumor's distance from its position from the left side of the tissue block. A set of values for the dimensions shown in FIG. 7 are listed in FIG. 7A. FIG. 7A shows the calculated plot of the pressure profile ratio ($\Delta P/P_o$) (the change in pressure of tumor tissue relative to normal tissue divided by the pressure sensed with no tumor) as a function of (X/L) along the X axis. This graph illustrates that a substantial change in the pressure profile ratio ($\Delta P/P_o$) of about 0.3 is observed when the tumor is a small distance (h=5 or 10 mm) from the tissue surface and that a smaller change in pressure profile ratio occurs when the tumor is far from the surface (e.g., h=30 mm). However, even when the tumor is deep (h=30 mm), the pressure profile ratio change is still readily discernible (with ($P/P_o$) about 0.1 which is quite measurable) to indicate a tissue abnormality at about X/L=0.70. The ratio of ($E/E_o$) is taken to be equal to 2.

Figure 8:
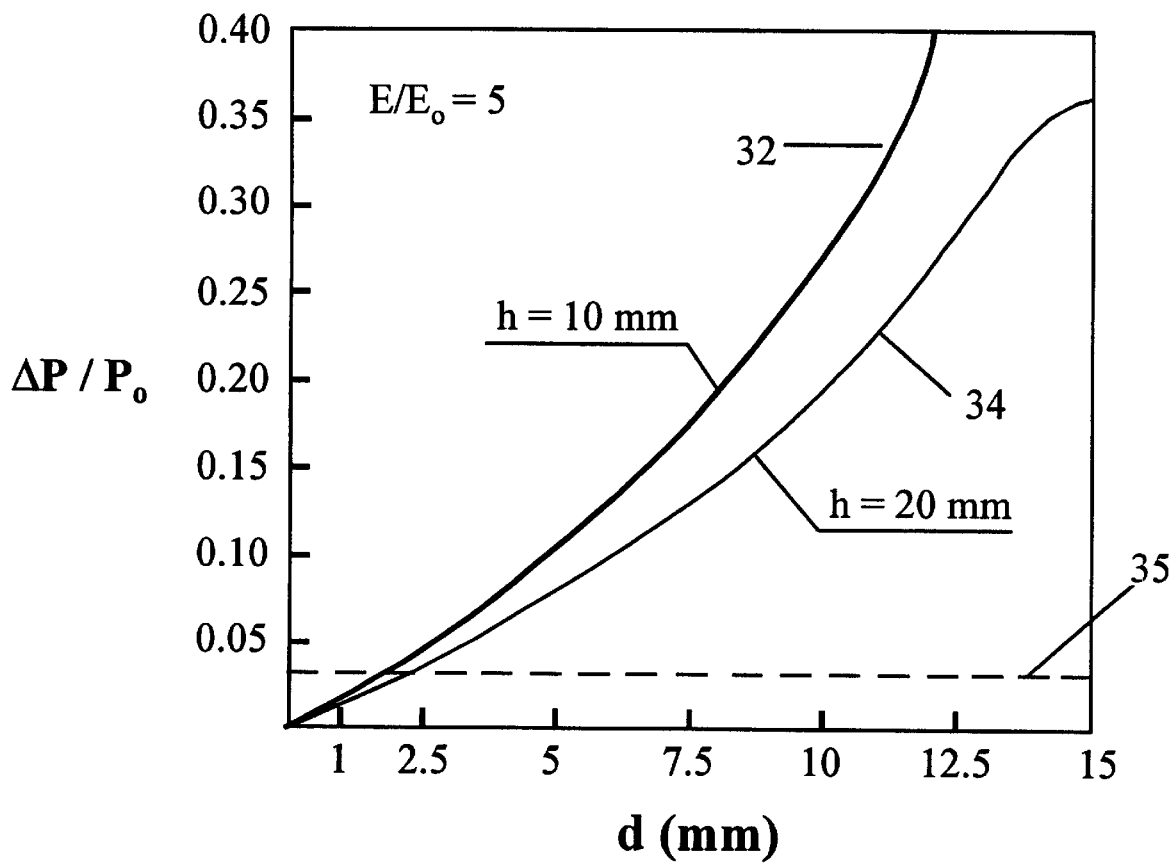
FIG. 8 is a graphical representation of calculated differential pressure ratio relative to the diameter of a tumor being sensed at differing depth of the tumor as shown in FIG. 5.

FIG. 8 illustrates the effect on the ability to ascertain a change in pressure with the sensors 15 as a function of the change in the diameter d of the tumor 30. As seen in FIG. 8, the elasticity moduli ratio ($E/E_o$) is equal to five, and the graph shows a plot of ($\Delta P/P_o$) versus d for a tumor with h=10 mm (indicated by line 32) and a tumor with h=20 mm (indicated by line 34). The pressure ratio ($\Delta P/P_o$) at the point of surface above the tumor, is indicated along the vertical axis, while the diameter of the tumor d is indicated along the horizontal axis.

The reference line indicated as 35 is more or less the base line for sensitivity of the ratio ($\Delta P/P_o$) measurement that can be easily obtained with existing pressure sensors. An accuracy of about three percent for pressure sensors is quite achievable, and the base line 35 represents a change of about three percent, which will give a clear indication of the presence of a tumor in normal tissue having a diameter (d) in the range of one to two millimeters. FIG. 8 indicates that, the larger the tumor, the greater is the change in the pressure ratio.

Figure 9:
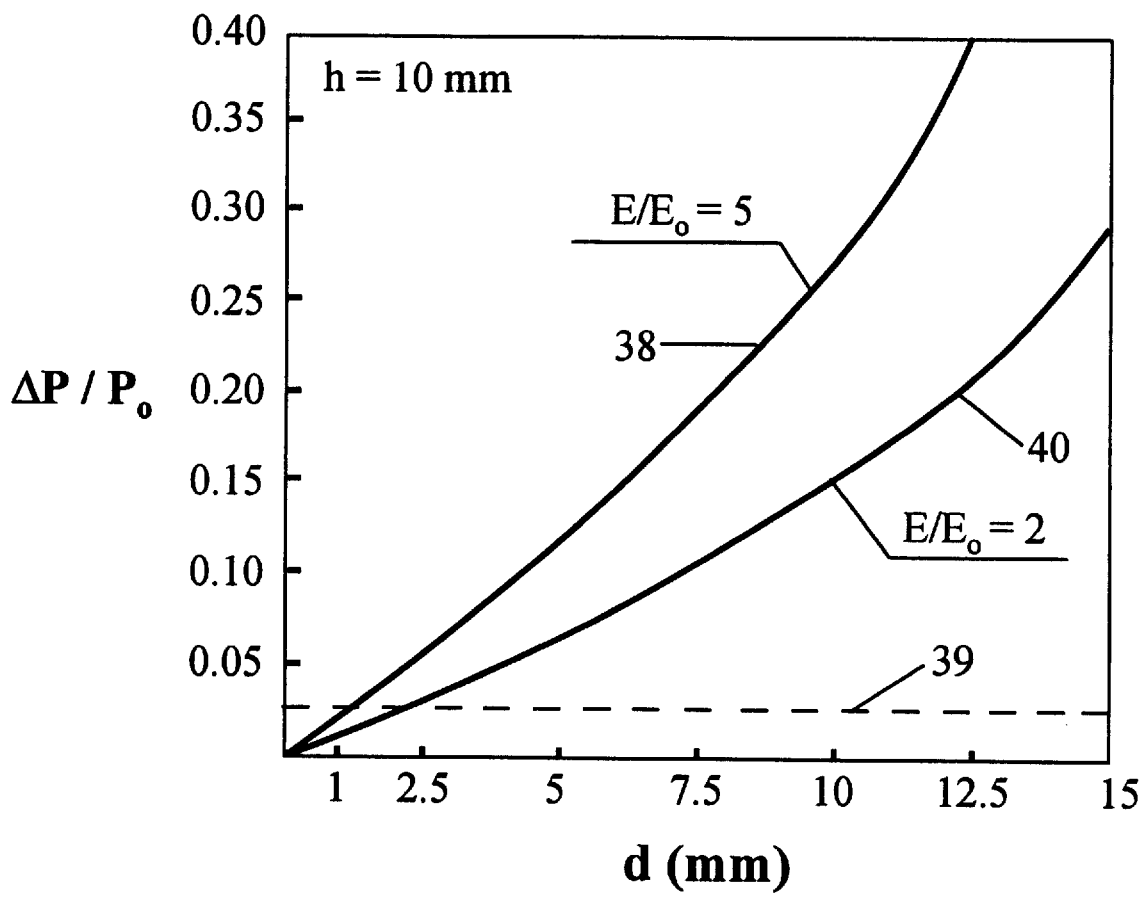
FIG. 9 is a graphical representation of the calculated differential pressure ratio relative to the diameter of a tumor, at differing ratios of moduli of elasticity between the surrounding tissue and the tumor.
Figures 10A, 10B, 10C:
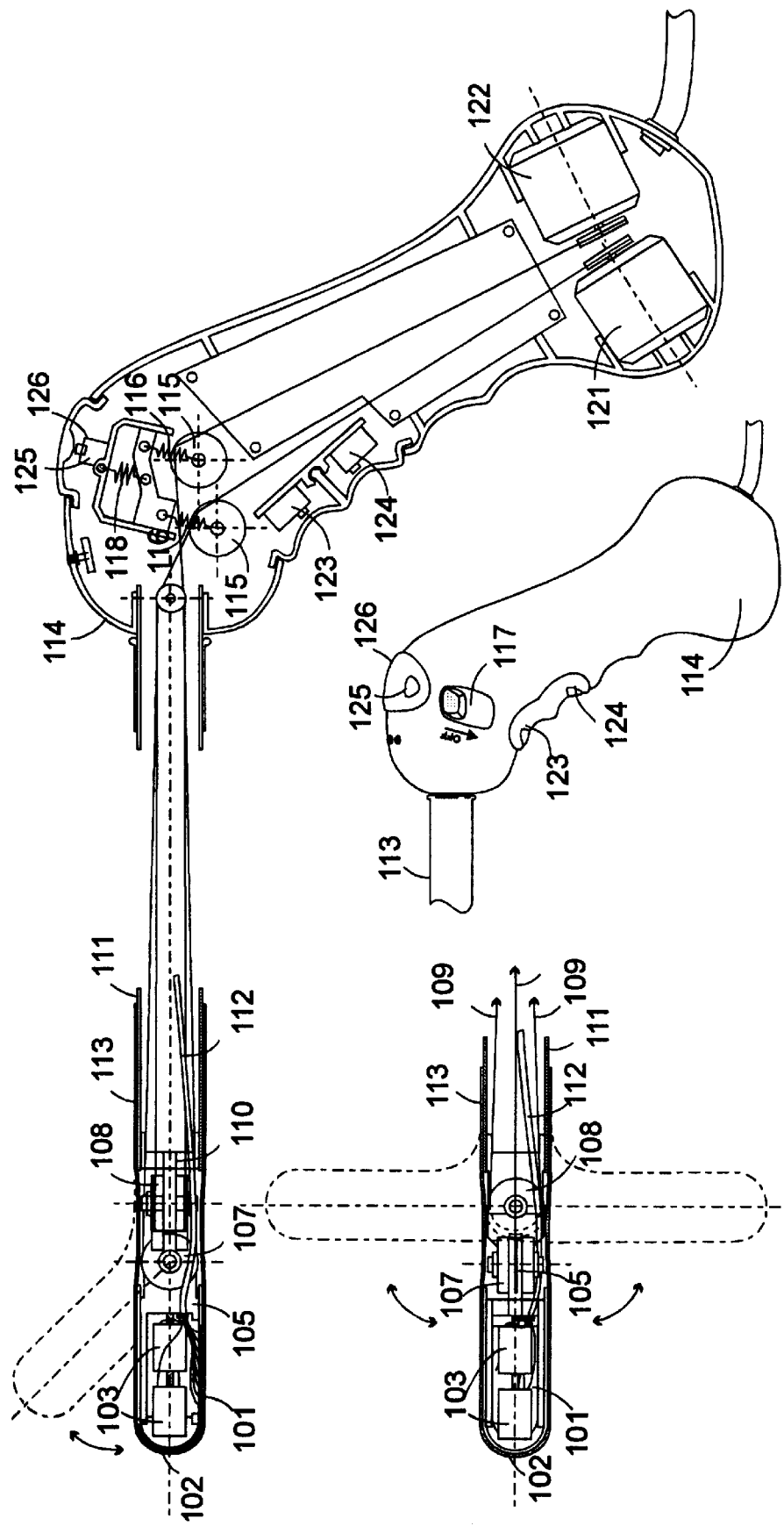
FIG. 10A is a side sectional view of a transrectal probe in accordance with the present invention.
FIG. 10B is a detail view of a pistol grip handle for a transrectal probe in accordance with the present invention.
FIG. 10C is the top view of an articulated probe tip.

FIG. 9 again illustrates the change in the pressure profile ratio ($\Delta P/P_o$) at the point of surface above the tumor as a function of the diameter (d) of the tumor. However, this time, the depth (h) of the tumor below the sensors 15 is set at 10 mm and a plot is provided for the case when the elasticity moduli ratio ($E/E_o$) equals 5 (indicated by upper curve 38) and when ($E/E_o$) equals 2 (indicated by lower curve 40). As expected, the greater the difference in the elasticity modulus between the tumor and surrounding tissue, (a larger ratio ($E/E_o$)), the more substantial change in the pressure profile ratio ($\Delta P/P_o$) for a given diameter tumor and the more easily the tumor will be detected. Taking the ratio ($\Delta P/P_o$) as an indication of sensitivity, one can observe line ($E/E_o$=5) crossing a threshold level of sensitivity (indicated by the dashed line at 39) indicating that detection of a tumor in the range of 1 mm can be made. When an elasticity modulus ratio is 2 (curve 40), one can observe that a tumor of 2.5 mm in diameter (d) could be detected. It is well known that palpation permits detection of tumors only if their diameter is over 8–10 mm, but not smaller. The graph in FIG. 9 shows quantitatively how the detection device (pressure sensors) becomes substantially more sensitive (on a relative basis, i.e., a larger change in the pressure profile ratio ($\Delta P/P_o$) is observed) as the elasticity moduli ratio ($E/E_o$) of the tumor tissue relative to the normal tissue increases.

FIGS. 10A–C, 11A–C, and 12A–C show sectional views and main elements of an alternative embodiment of the transrectal Mechanical Imaging probe. Referring to the longitudinal view of the probe 100 shown in FIG. 10A, the probe 100 comprises a moveable tip 102 which contains an array of pressure sensors 101 and a position/orientation sensor 103 (sensing element of the 3SPACE® INSIDE-TRAK™ position/orientation tracking device made by Polhemus Inc., Colchester, Vt.). The resolution of the 3D position measurements achievable with this particular system is 0.1 mm, assuming that the maximum distance between the main electronic unit (fixed outside the probe) and the sensing element 103 (mounted inside of the tip 102 of the probe 100) is no more than 50 cm. The tip 102 of the probe 100 can be made significantly thinner than a finger of a physician. The tip 102 is mated to a rigid tube 111, which in turn is attached to a pistol grip handle 114. A disposable rubber sheath 113 covers the entire tip 102 as well as the tube 111. The electrical connections for the pressure sensor array as well as the position sensor are carried via a cable 112 (partly shown). A flexible joint between the tip 102 and the tube 111 shown in detail in FIG. 12 is provided to allow the tip to be articulated over angles ranging from 0 to ±45 vertically, and ±90 horizontally. The joint consists of disks 105 and 107 which allow vertical motion, and disks 108 and 110 which allow horizontal motion. Two stepper motors 121 and 122 within the handle drive control cables 106 and 109, thereby permitting positioning of the probe tip 102, based on operator commands. The probe 102 tip position is controlled by pressing the various buttons on the handle 114, a two-position switch for up/down 123, 124, and another two-position switch for left/right operation 125, 126. In addition to the stepper motors, the handle also contains a printed circuit board (PCB) with all electronics necessary for operating the motors, as well as a first stage of the data acquisition circuit. The control cables 106 and 109 are tensioned by two rollers 115 connected to tensioning springs 116. The springs 116 are mounted on a safety switch 117 which is connected to the handle via a safety spring 118. The resistance of the spring 118 is calibrated so that the forces experienced by the patient can never exceed certain safe limits. The operator can manually release the tension of the cables 106 and 109 by pulling on the safety switch 117 if there is any indication that the patient is experiencing discomfort or pain. In addition to this mechanical safety mechanism, it also is possible to use a sensor which will monitor the tension of the springs 116 and which will stop the motion of the stepper motors 121 and 122 if a preselected level of tension is reached. Alternatively, a biopsy needle (not shown) can be provided on the probe 100 for taking a tissue sample.

FIGS. 11A–C and 12A–C are detail views of the probe tip and the joint which permits articulation of the probe tip. The pressure sensor 101 for use in the prostate transrectal probe 100 employs a polyvinylidene fluoride (PVDF) piezoelectric film (such as manufactured by AMP Inc., Valley Forge, Pa.). Other pressure sensors may be used. However, the PVDF film pressure sensors are highly sensitive, easy to work with, provide excellent matching with soft biological tissue and are readily available. There are several ways in which the PVDF film can be mounted on the tip 102 of the transrectal probe 100 to serve as a pressure sensor. In one of the possible patterns of the sensor arrangement (FIG. 11C), there are two long 1×12 mm sensors on each side of the array. These are used together with two end sensors in the row of 6 2.5×5 mm to provide information. This information is displayed to the operator so that he or she can adjust the position of the sensor during examination to provide a more even pressure distribution. It can also be used to filter out those points of the collected data which were obtained with the array tilted relatively to the surface of the prostate.

Figure 13:
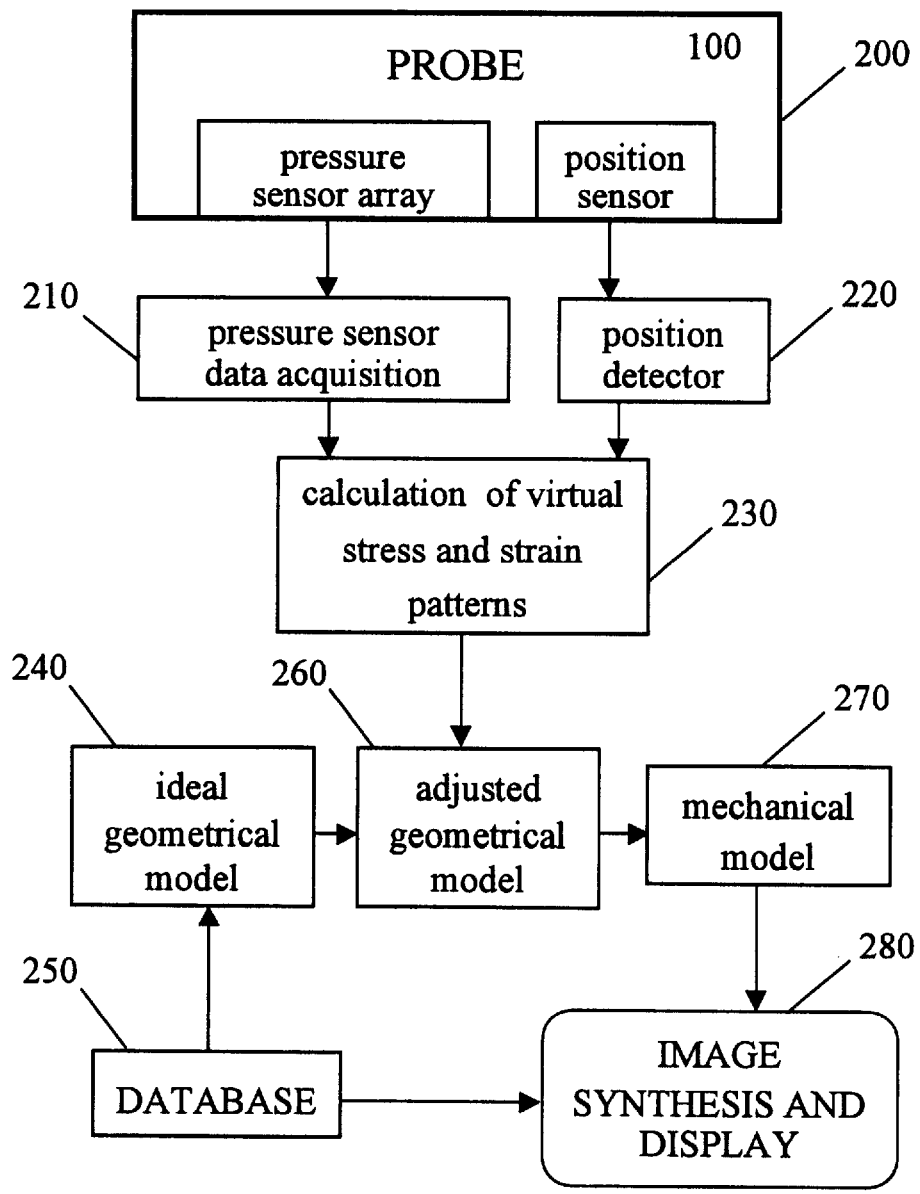
FIG. 13 is a schematic diagram of the method and apparatus in accordance with the present invention.

FIG. 13 is a schematic diagram showing the processing of signals 200 from the probe 100. Pressure sensor data 210 and position/orientation sensor data 220 are combined for calculating the virtual patterns of stress and strain 230. An ideal geometrical model 240 of the prostate is generated from a database 250 and is further adjusted to match the estimated dimensional parameters of the examined prostate. Using this adjusted geometrical model 260 theoretical patterns of stress and strain are evaluated and compared with the respective virtual stress and strain patterns, with the differences being used to create a mechanical model 270 of the prostate. This mechanical model with addition of relevant data from the database is used to create and display an image 280.

Figure 14A:
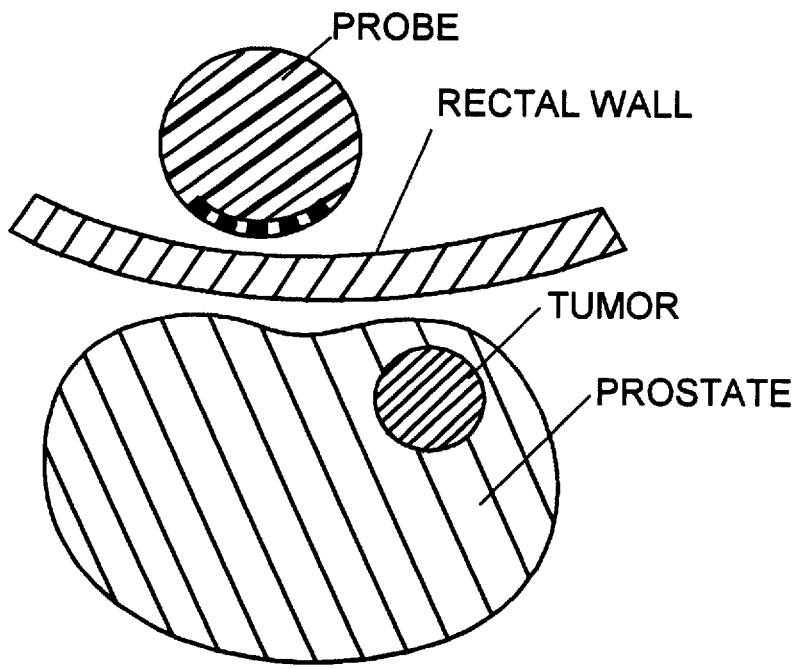
FIG. 14A is a sectional view showing the relationship of the probe, rectal wall, and prostate with internal nodule.
Figure 14B:
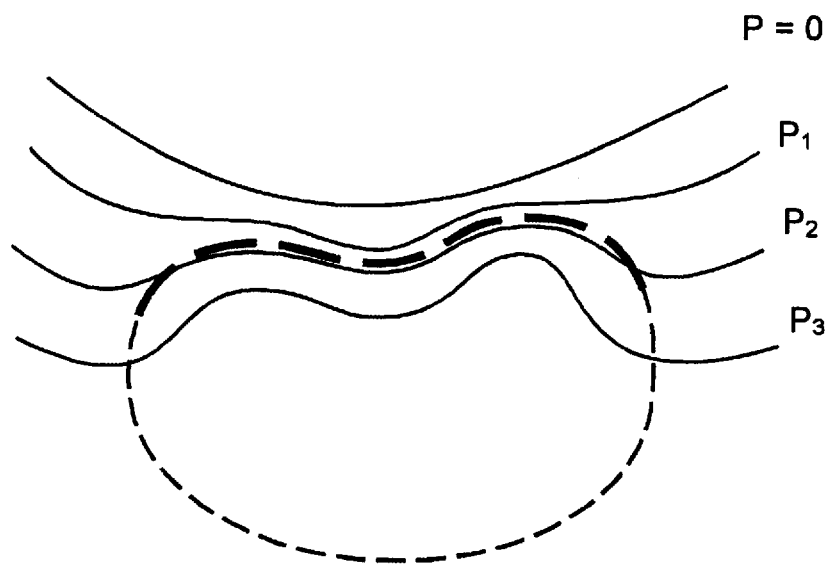
FIG. 14B is a schematic diagram showing virtual lines of equal pressure calculated from the data obtained using the position sensor and pressure sensor array of the present invention.
Figure 19:
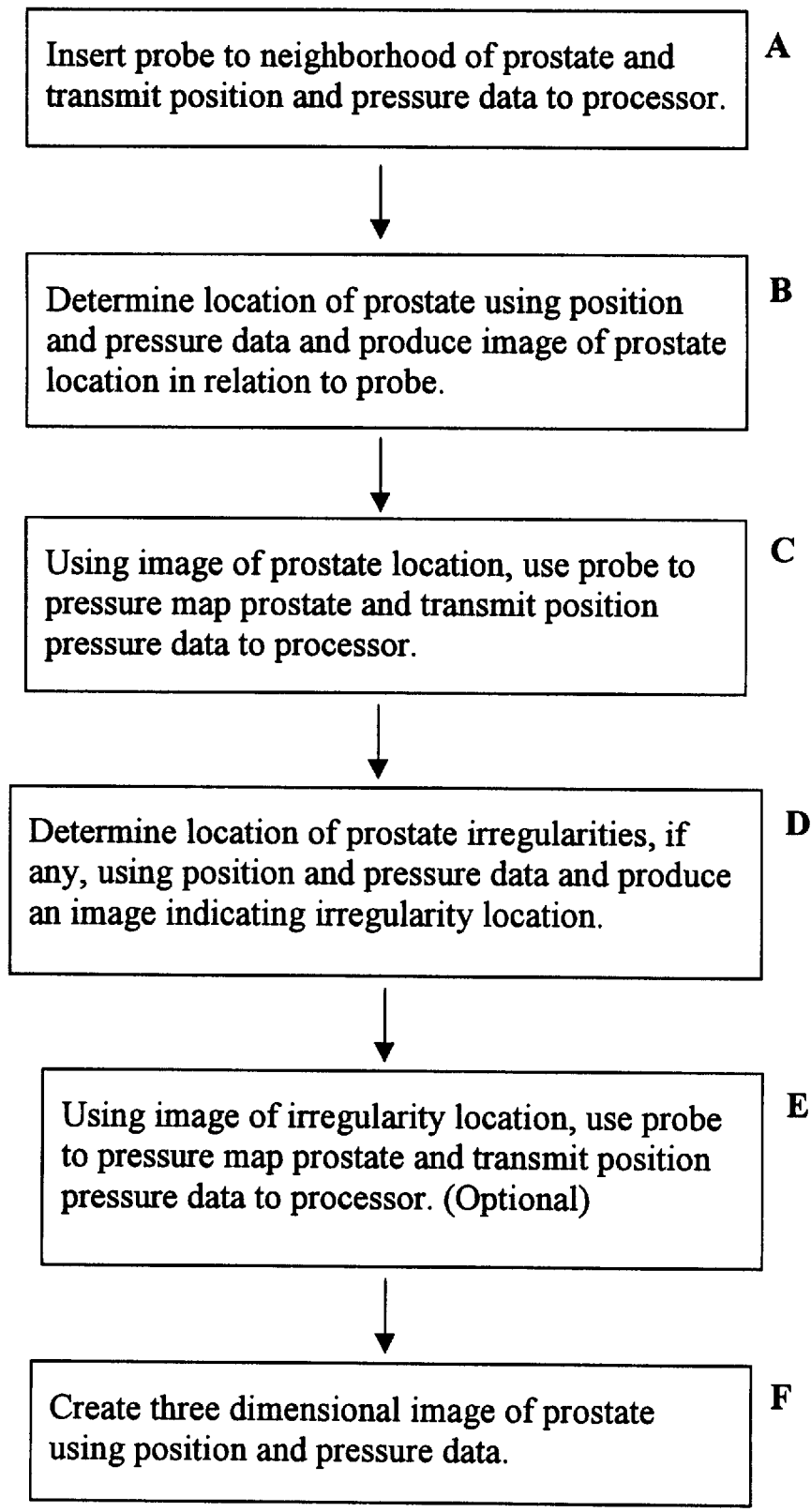
FIG. 19 is a schematic flow diagram of the data acquisition steps in imaging a prostate.

FIG. 14A shows the relationship of the probe, rectal wall, and a prostate with a nodule in cross section. FIG. 14B illustrates the virtual lines of equal pressure calculated from the data obtained by the position sensor and pressure sensor array. Equal pressure lines denoted in FIG. 14B as P=0, $P_1$, $P_2$, and $P_3$ which correspond to different levels of pressure, are related to the virtual strain profile. A fraction of the prostate contour shown in FIG. 14B by the bold dotted line is reconstructed using the equal pressure profile data and the nonlinearity of the strain/stress relationship. At low level of pressures when the compression is related mainly to the motion of the rectal wall tissue the system behaves linearly. At a certain level of compression the slope of the strain/stress curve exhibits sharp increase reflecting the resistance of the prostate tissue. In each region over the prostate there is a point in the space where the strain/stress relationship starts to change sharply its slope. The surface formed by these points corresponding to a certain level of nonlinearity of the strain/stress relationship is determined by the geometrical parameters of the examined prostate and can be used for estimating the contour of the prostate shown in FIG. 14B by dotted line. The data shown schematically in the FIG. 14B can also be used to evaluate the virtual stress pattern. The virtual stress pattern is obtained by calculating the pressure gradients for the points on the surface shown by dotted line. Both virtual strain and virtual stress profiles are further used to form a mechanical model of the examined prostate using additionally relevant information from a general database, as shown in FIG. 13. Referring to the drawings, FIG. 19 is a schematic flow diagram showing the preferred steps involved data acquisition. The first step, shown in block A, is to insert the probe into the rectum to the neighborhood of the prostate and to transmit position and pressure data from the probe to the processor.

Figure 20:
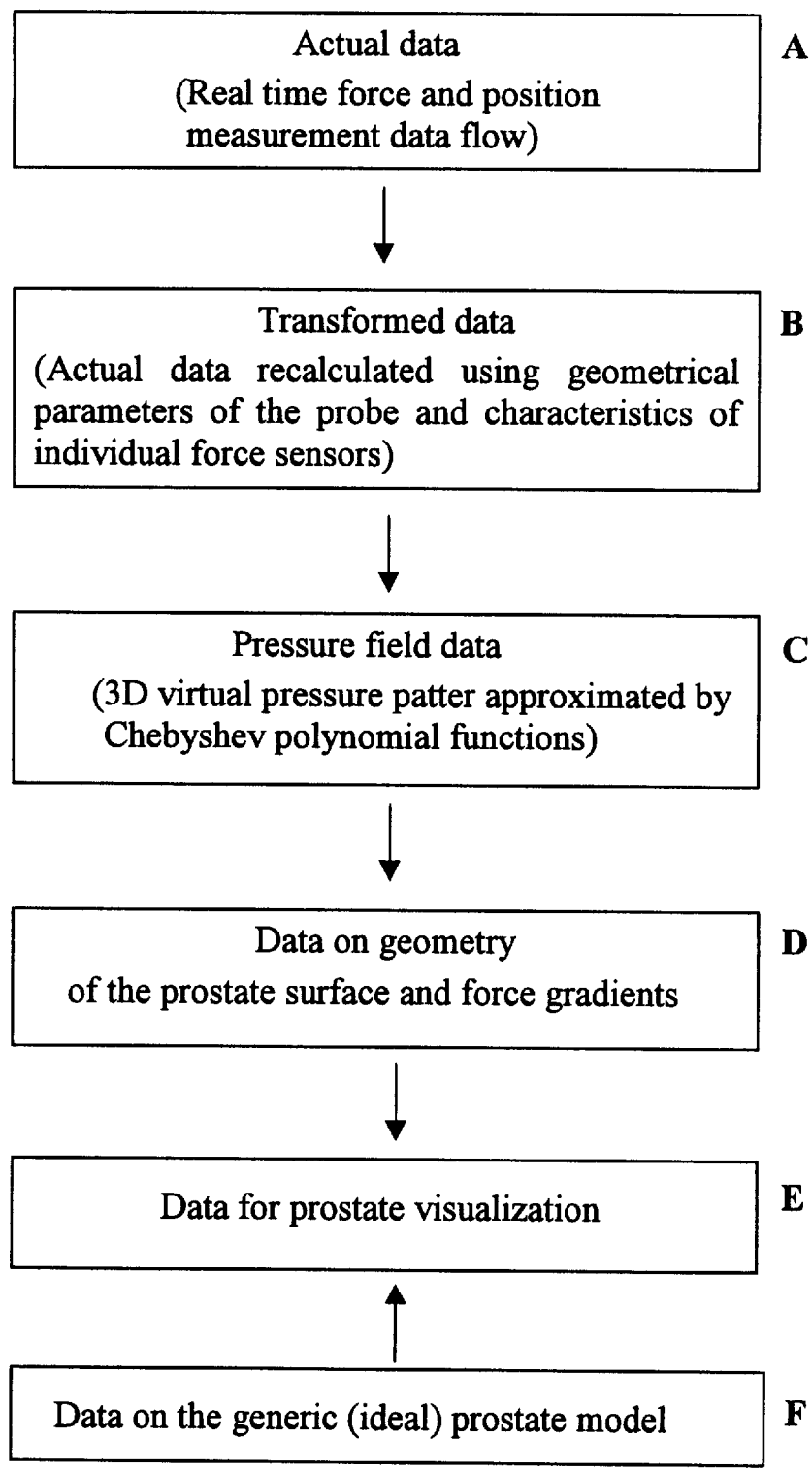
FIGS. 20A–20F illustrate computer displays during steps of the preferred embodiment of the method.

In the preferred embodiment, the processor can display an image of typical pelvic anatomy and the position of the probe in relation to the anatomy along with a designation of the region to be scanned with the probe. FIG. 20A shows a representative image with the entering probe location shown as a white area and the region to be scanned ("bleared") designated by a dashed-line rectangle (a "window" to be cleared).

The next step shown in block B of FIG. 19 is to determine the location of the prostate in the test subject using position and pressure data and to produce an image of the prostate in relation to the probe.

In the preferred embodiment, the prostate is located by manipulating the probe to scan the region in the image window. The initial image on the computer screen at the beginning of this phase can be a vague representation of the prostate and pelvic anatomy. This initial image serves as a map to navigate the probe. A cursor on the screen can represent the tip of the examining probe.

The position feedback on the computer screen helps the user adjust manipulation of the probe. The pressure exerted by the operator and the rate of movement of the probe can be indicated on the screen to direct and optimize operator performance. The color of the cursor can be changed to indicate whether the pressure being applied is insufficient, excessive or adequate to optimally image the prostate. If the probe is being moved too fast, a warning signal can be placed above the image on the screen. Similarly, if the probe is misoriented so that less than all the sensors contact tissue, an appropriate misorientation message can be displayed.

The computer display can show the motion of the probe in the window by clarifying the examined part of the initially vague image. FIG. 20B shows the window nearly cleared with typical features of the region, including the prostate, located relative to the probe. Note that the instruction to the operator: "Scan the window until clear" is presented adjacent the image screen.

When the operator clears the window, an "End of task" signal can be sent to the processor by depressing a switch on the probe control handle. Alternatively, the processor can be programmed to recognize that the window has been cleared.

Upon clearing of the window, the processor can calculate the position of the center and boundaries of the prostate, thereby permitting the image on the screen to correctly show the relative position of the probe with respect to the actual prostate. These calculations take about 10–15 seconds, after which the image on the screen can zoom out to reveal the prostate and neighboring structures. FIG. 20C illustrates such transition zooming, with the prostate shown centered between the pelvic bones. After this enlarged image of the prostate appears on the screen the process moves into phase 2.

The next step (block C of FIG. 19) involves using the image of the prostate location and the probe to pressure map the prostate and transmit position and pressure data to the processor.

In the preferred embodiment, the processor program displays a sequential list of regions of the prostate to be examined adjacent the image screen, and the operator performs this sequence of operations. Advantageously, the choice of this sequence is similar to that of a regular digital rectal examination so that it is familiar to the operator. After completion of each step of the sequence, the operator can send an "End of Task" signal, and the processor can check the task on the display and highlight the next task in the sequence. FIG. 20D shows a typical image of the prostate and taskbar.

The fourth step shown in FIG. 19, block D, is to determine whether there are irregularities in the prostate using the data acquired and, if so, to produce an indication of the locations of the irregular regions such as by marking the regions on the prostate image. To further reveal areas in the prostate that are suspicious and require more detailed examination, a second reference image can be simultaneously displayed. The reference image can be a computer simulated ideal normal prostate or an image of the prostate of the same patient obtained in a previous examination. FIG. 20E illustrates a typical split screen display showing the calculated model and reference model in the right-hand portion of the computer display along with the operator directive: "Examine areas of increased hardness".

The next step, which is optional, is to use the probe to further pressure map the regions of irregularity and transmit the additional data to the processor. Based on the differences between the examined and the referenced prostates, the operator makes a decision on the desirability of collecting additional data in the regions of interest. Such collection may take an additional 1 or 2 minutes, after which the operator can terminate the examination as by pressing the "End of task" button and removing the probe from the patient.

In the final step, the computer calculates a virtual pressure pattern similar to that shown in FIG. 14B preferably using all the data collected. Then based on this virtual pressure pattern, the computer calculates a three-dimensional mechanical model of the prostate and finally, it generates a three-dimensional image of the examined prostate. It displays the examined prostate and preferably displays a reference prostate. An additional advantageous feature is the ability to rotate the image of the reconstructed prostate on the screen, as by using an associated computer mouse. The computer can synchronously rotate the reference prostate to facilitate comparison and detection of abnormalities.

The preferred method of preparing a three-dimensional image of the prostate can be better understood by considering the data flow chart of FIG. 21. The first set of data in block A is actual data collected by the probe. It constitutes a flow of real time force measurements from the pressure sensors and position measurements from the position sensor. In the most general case, it involves six position parameters (3 coordinates of the position sensor and 3 angles describing the tilt of the probe tip) and pressure data from every pressure sensor.

The set of actual data is processed to a set of transformed data shown in block B of FIG. 21. By elementary geometrical processing, the actual position data permits determination of three spatial coordinates for each pressure sensor. Thus, one can relate every measured force value from each sensor to a point in three-dimensional space. The force measured by the sensor and its three coordinates are the transformed data.

The transformed data can now be processed to provide pressure field data shown in block C. The transformed data contains both useful information about parameters of the tissue being investigated and noise of various origins. The noise originates from force and position measurement error and from artifacts related to tissue movement (movement of the prostate, movement of the patient). Pressure field data is calculated by processing the transformed data to minimize noise and extract the 3D spatial distribution of pressure approximating ideal conditions of measurement. While there are a number of possible algorithms for this processing, the preferred approach is to use Chebyshev approximation (polynomial approximation from Chebyshev coefficients) as described by J. P. Boyd in *Chebyshev and Fourier Spectral Methods,* Springer Verlag (New York, 1989) and presented in algorithmic form by W. H. Press et al., *Numerical Recipes in C,* pp. 190–198 (Cambridge U. Press, 1996), both of which are incorporated herein by reference. The pressure field is represented as a superposition of Chebyshev polynomial functions.

The pressure field data can be processed to provide data on the geometry of the prostate surface and force gradients shown in block D. Having approximated (above) smooth surfaces of equal pressure, one can calculate geometrical parameters and hardness of the prostate. The surface of the examined prostate can be obtained by choosing a level of force corresponding to deformation of the rectal wall that permits the sensors to press against the prostate surface. From the pressure gradients, information on the prostate tissue hardness can be generated.

From the pressure field data approximated by Chebyshev polynomials, one can now reconstruct a three-dimensional elasticity model of the prostate—a model which will show the distribution of hardness in three-dimensional space. While there are a number of ways of calculating this model from the pressure field, the preferred method is 3D reconstruction based on the finite element method described by G. Strang et al., *An Analysis Of The Finite Element Method* (Prentice Hall, 1973) and D. S. Burnett, *Finite Element Analysis: From Concepts To Applications* (Addison-Wesley, 1987), both of which are incorporated herein by reference.

A convenient way to produce an image from the calculated model is to store an image of an ideal prostate and to deform the ideal image to conform to the calculated model using image modification techniques well known in the art. Advantageously, irregularities can be indicated on the image to assist diagnosis.

In traditional medical imaging, the device usually displays the structure of an object in terms of some measured physical property. The image obtained this way is often very far from what the actual examined region of body or an organ would look like if exposed to direct sunlight, or drawn by an artist. Therefore, an expert in a particular type of image analysis is required to tell the physician what information from the image is relevant to the diagnosis. Currently, as a result of a wider use of powerful computer means and databases, an alternative approach to imaging, so called Knowledge-Based Imaging (Sarvazyan et al., *A new philosophy of medical imaging,* Medical Hypotheses 36, 327–335, 1991, incorporated herein by reference) has started to emerge. The method of the present invention includes the use of the knowledge-based approach briefly described below. Using knowledge-based imaging, a computer can store in memory a 3D picture of a "normal" prostate which is being examined, and adjust (transform) this image according to the measured data, to produce an image that represents the actual examined gland. Such a pictorial 3D image or its cross sections will additionally include data on the mechanical properties of the prostate. It will be significantly easier for a physician to recognize abnormalities of the examined organ, represented on such an image. Further, the expert system will use the knowledge about characteristics of different types and stages of prostate cancer to point out any poorly defined and suspicious regions in the model, or just show any abnormalities or deviations from what the "normal" prostate should look like. At this point, the physician can also enter into the computer new information based on other tests or exams performed on the same prostate, and the knowledge base will "learn" and "expand."

Once a 3D model of the actual examined prostate is stored in the computer, it must be presented by the user in a way that would allow both external and internal features to be seen on one picture. This means that the 3D image on the screen should contain information about geometrical features of the prostate as well as spatial distribution of elasticity and surface texture information. Additionally, the image should indicate to the user which areas of the examined prostate are poorly defined and need to be examined further in order to produce a complete diagnosis. There are several potential 3D visualization methods that can be suitable for this task, such as polygon based surface methods, ray cast volume rendering and cross section slicing.

Although certain presently preferred embodiments of the present invention have been specifically described herein, it will be apparent to those skilled in the art that variations and modifications of the various embodiments shown and described herein may be made without departing from the spirit and scope of the invention. Accordingly, it is intended that the invention be limited only to the extent required by the appended claims and the applicable rules of law.

I claim:

1. A transrectal probe for measuring mechanical properties of the prostate gland comprising:
   a control handle;
   a probe shaft having an axis, said shaft extending from said handle; and
   a tip at the end of said shaft for pressing against tissue overlying surfaces of the prostate gland, said tip comprising a position sensor for measuring the position of said tip and an array of force sensors for measuring a pattern of pressure when said tip is pressed against said tissue.

2. The transrectal probe of claim 1 wherein the tip is movable above and below the axis of said probe shaft.

3. The probe of claim 2 wherein said tip is covered by a disposable sheath of soft, flexible material.

4. The probe of claim 2 wherein said tip and at least a portion of said shaft is covered by a disposable sheath of soft, flexible material.

5. The probe of claim 1 further comprising paths for transmitting signals said from said position sensor and the pattern of pressure detected by said array to a signal processor.

6. The probe of claim 5 wherein said control handle comprises a switch for controlling input from said position sensor and said array of force sensors to a computer interface.

7. The probe of claim 1 wherein said control handle comprises a pistol grip handle.

8. The probe of claim 1 wherein said force sensors comprise bending beam force sensors.

9. The probe of claim 1 wherein said array of pressure sensors is formed of a left row of said pressure sensors and a right row of said pressure sensors, said left row of said pressure sensors measures pressure applied against the left surface of said tip and said tip and said right row of said pressure sensors measures pressure applied against the right surface of said tip.

* * * * *